(12) United States Patent
Wilson et al.

US012318487B2

(10) Patent No.: US 12,318,487 B2
(45) Date of Patent: Jun. 3, 2025

(54) SOLID TABLET DOSAGE FORM OF RIDINILAZOLE

(71) Applicant: c/o Summit (Oxford) Limited, Abingdon (GB)

(72) Inventors: Francis X. Wilson, Welwyn Garden (GB); Laura Trespidi, Bramley Tadley Basingstoke (GB); Jean-Francois Carniaux, Abingdon (GB); Peter Timmins, Ellesmere Port (GB)

(73) Assignee: SUMMIT (OXFORD) LIMITED, Abingdon (GB)

( * ) Notice: Subject to any disclaimer, the term of this patent is extended or adjusted under 35 U.S.C. 154(b) by 610 days.

(21) Appl. No.: 17/576,242

(22) Filed: Jan. 14, 2022

(65) Prior Publication Data
US 2022/0226249 A1    Jul. 21, 2022

(30) Foreign Application Priority Data
Jan. 14, 2021   (GB) ..................................... 2100470

(51) Int. Cl.
*A61K 9/14* (2006.01)
*A61K 9/20* (2006.01)
*A61K 31/444* (2006.01)

(52) U.S. Cl.
CPC .......... *A61K 9/2077* (2013.01); *A61K 9/2018* (2013.01); *A61K 9/2054* (2013.01); *A61K 9/2095* (2013.01); *A61K 31/444* (2013.01)

(58) Field of Classification Search
CPC . A61K 9/14; A61K 9/141; A61K 9/16; A61K 9/1605; A61K 9/1652; A61K 9/20; A61K 9/2004; A61K 9/2009; A61K 9/2018; A61K 9/205; A61K 9/2056; A61K 9/2054; A61K 9/2059; A61K 9/2086
See application file for complete search history.

(56) References Cited

U.S. PATENT DOCUMENTS

| | | | |
|---|---|---|---|
| 5,824,698 | A | 10/1998 | Hasler et al. |
| 2007/0112048 | A1 | 5/2007 | Bavari et al. |
| 2010/0204292 | A1 | 8/2010 | Aurora et al. |
| 2016/0184283 | A1 | 6/2016 | Wilson et al. |
| 2022/0289705 | A1 | 9/2022 | Wilson et al. |

FOREIGN PATENT DOCUMENTS

| | | | |
|---|---|---|---|
| WO | WO 2002060879 A2 | 8/2002 | |
| WO | WO 2003/105846 A1 | 12/2003 | |
| WO | WO 2004/041209 A2 | 5/2004 | |
| WO | WO 2006/076009 A2 | 7/2006 | |
| WO | WO 2007/056330 A1 | 5/2007 | |
| WO | WO 2007/148093 A1 | 12/2007 | |
| WO | WO 2010/063996 A2 | 6/2010 | |
| WO | WO 2011/151620 A1 | 12/2011 | |
| WO | WO 2011/151621 A1 | 12/2011 | |
| WO | WO-2016120258 A1 * | 8/2016 | ............. A61K 31/47 |
| WO | WO-2019068383 A1 * | 4/2019 | ............ A61K 31/444 |
| WO | WO 2021/009514 A1 | 1/2021 | |

OTHER PUBLICATIONS

International Search Report and Written Opinion for Application No. PCT/IB2022/050311, mailed Apr. 5, 2022, 13 pages.
International Search Report and Written Opinion for Application No. PCT/GB2020/051710, mailed Nov. 23, 2020, 13 pages.
Bhattacharya, S. and P. Chaudhuri (2007) "Metal-Ion-Mediated Tuning of Duplex DNA Binding by Bis(2-(2-pyridyl)-1H-benzimidazole)" Chem Asian J, 2:648-655.
Bowser, T. E. et al. (2007) "Novel anti-infection agents: Small-molecule inhibitors of bacterial transcription factors" Bioorganic & Medicinal Chemistry Letters 17:5652-5655.
Caira, M.R. (1998) "Crystalline Polymorphism of Organic Compounds" Topics in Current Chemistry, 198:163-208.
Chaudhuri, P. et al. (2007) "An Experimental and Computational Analysis on the Differential Role of the Positional Isomers of Symmetric Bis-2-(pyridyl)-1H-benzimidazoles as DNA Binding Agents" J Org Chem, 72:1912-1923.
Singh, M.P. et al. (2000) "Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives" Synthesis, 10:1380-1390.
Vickers, R.J. et al. (2017) "Efficacy and safety of ridinilazole compared with vancomycin for the treatment of Clostridium difficile infection: a phase 2, randomised, double-blind, active-controlled, non-inferiority study" Lancet Infect Dis, 17:735-744.
Search Report issued in Great Britain Patent Application No. GB2100470.0, dated Nov. 26, 2021, with letter (4 pages).
Bertolini, G. et al. (1997) A New Rational Hypothesis for the Pharmacophore of the Active Metabolite of Leflunomide, a Potent Immunosuppressive Drug. J Med Chem, 40:2011-2016.
Englebienne, P. (2005) Effects of Introducing Silicon Isosteres in COX-2 Inhibitors: A Preliminary In Silico Evaluation. Med Chem, 1(3):215-226.
Ghadi, R. and N. Dand (2017) BCS class IV drugs: Highly notorious candidates for formulation development. J Control Rel, 248:71-95.
Huang, W.X. et al. (2006) Elimination of metformin-croscarmellose sodium interaction by competition. Int J Pharm, 311(1-2):33-39.

(Continued)

*Primary Examiner* — Micah Paul Young
(74) *Attorney, Agent, or Firm* — Birch, Stewart, Kolasch & Birch, LLP

(57) ABSTRACT

The present invention relates to solid tablet oral dosage forms of 2,2'-di(pyridin-4-yl)-1H,1'H-5,5'-bibenzo[d]imidazole (which may also be known as 2,2'-di-4-pyridinyl-6,6'-bi-1H-benzimidazole; 5,5'-bis[2-(4-pyridinyl)-1H-benzimidazole]; 2,2'-bis(4-pyridyl)-3H,3'H-5,5'-bibenzimidazole; or 2-pyridin-4-yl-6-(2-pyridin-4-yl-3H-benzimidazol-5-yl)-1H-benzimidazole), referenced herein by the INN name ridinilazole, and pharmaceutically acceptable derivatives, salts, hydrates, solvates, complexes, bioisosteres, metabolites or prodrugs thereof.

39 Claims, 20 Drawing Sheets

(56) References Cited

OTHER PUBLICATIONS

Kushner, D.J. et al. (1999) Pharmacological uses and perspectives of heavywater and deuterated compounds. Can. J Physiol Pharmacol, 77(2):79-88.

Remington, J. (Jan. 2012) Chapter 45: Oral solid dosage forms. In Remington: The Science and Practice of Pharmacy, 22nd. Ed. p. 947.

Tacke, R. and H. Zilch (1986) Sila-substitution—a useful strategy for drug design? Endeavour, New Series. 10(4):191-197.

Ayupova et al., "State Educational Institution of Higher Professional Education "Bashkir State Medical University of the Federal Agency for Healthcare and Social Development of the Russian Federation" Institute of Postgraduate Education," Biopharmacy, 2011, 5 pages total, with English translation.

Morissette et al., "High-throughput crystallization: polymorphs, salts, co-crystals and solvates of pharmaceutical solids," Advanced Drug Delivery Reviews, vol. 56, 2004, pp. 275-300.

Pertseva et al., "Pharmaceutical and Biomedical Aspects of Drugs," Ministry of Health of Ukraine, Ukrainian Pharmaceutical Academy, vol. 1, Chapter 11, 1999, pp. 253-254 (5 pages total), with English translation.

Shotton et al., "Effect of Intragranular and Extragranular Disintegrating Agents on Particle Size of Disintegrated Tablets," Journal of Pharmaceutical Sciences, pp. 1170-1174.

Vandana et al., "An overview on in situ micronization technique—An emerging novel concept in advanced drug delivery," Saudi Pharmaceutical Journal, vol. 22, 2014, pp. 283-289.

* cited by examiner

FIG. 15

Bristol Stool Chart

| Type 1 | ● ● ● ● ● ● ● | Separate hard lumps, like nuts (hard to pass) |
|---|---|---|
| Type 2 | | Sausage-shaped but lumpy |
| Type 3 | | Like a sausage but with cracks on its surface |
| Type 4 | | Like a sausage or snake, smooth and soft |
| Type 5 | | Soft blobs with clear-cut edges (passed easily) |
| Type 6 | | Fluffy pieces with ragged edges, a mushy stool |
| Type 7 | | Watery, no solid pieces. Entirely Liquid |

FIG. 19

| Ingredients | PROCESS | In Process Controls |
|---|---|---|
| API<br>Lactose monohydrate 200M<br>MCC PH101<br>HPC EXF<br>Croscarmellose sodium | Note: Sieve excipients only through 1000 µm screen. API has been sieved only for Batch 1804. | |
| | Premix in Diosna P1-6, 1 L bowl for 5 minutes<br>125 rpm | Initial loss on drying. IR moisture balance set at 80°C with automatic end mode. Bulk & tapped density and flow of blend |
| Purified water<br>Target 25-35% of batch size, depending on the batch. More details on the composition tables. | Spray into granulator<br>Impeller 125 rpm<br>Chopper 2200 rpm<br>Spray rate varied to allow granulation time of 5 minutes. | Granule appearance |
| | Wet Massing<br>1 minute<br>Impeller 125 rpm<br>Chopper 2200 rpm | |
| | Dry in Endecotts fluid bed dryer at 60°C for 30 mins. | Final loss on drying. IR moisture balance set at 90°C with automatic end mode. Target within 0.5% of initial value. Prior to milling, perform PSD, friability (if appropriate), bulk & tapped density, flow properties and appearance. |
| | Mill using 1143 µm screen<br>Calculate available milled granules | Post-milling, perform PSD, bulk & tapped density, flow properties and appearance. Take 10 g as a retain for granule friability |
| Lactose monohydrate 100M (200M for Batch 1801)<br>MCC PH102 (PH101 for Batch 1801)<br>Croscarmellose sodium | Re-calculate the required extra excipients based on available milled granules.<br>Sieve excipients through 1000 µm screen<br>Blend at 25 rpm for 3 minutes : 5 L shell, Turbula blender | |
| Magnesium stearate | Screen (250 µm sieve)<br>Blend on a Turbula blender at 25 rpm for 3 minutes | Flow, particle size distribution |
| | Compress 14.5 x 5.75 mm tooling<br>(400 mg fill weight) | Appearance, tablet weight/weight variation, hardness, thickness and friability |

SOLID TABLET DOSAGE FORM OF RIDINILAZOLE

CROSS REFERENCE TO RELATED APPLICATIONS

This application claims priority to GB Patent Application No. 2100470.0, which was filed Jan. 14, 2021, the entire contents of which are incorporated by reference herein.

FIELD OF THE INVENTION

The present invention relates to solid tablet oral dosage forms of 2,2'-di(pyridin-4-yl)-1H,1'H-5,5'-bibenzo[d]imidazole (which may also be known as 2,2'-di-4-pyridinyl-6,6'-bi-1H-benzimidazole, 5,5'-bis[2-(4-pyridinyl)-1H-benzimidazole], 2,2'-bis(4-pyridyl)-3H,3'H-5,5'-bibenzimidazole or 2-pyridin-4-yl-6-(2-pyridin-4-yl-3H-benzimidazol-5-yl)-1H-benzimidazole), referenced herein by the INN name ridinilazole, and pharmaceutically acceptable derivatives, salts, hydrates, solvates, complexes, bioisosteres, metabolites or prodrugs thereof.

BACKGROUND OF THE INVENTION

Infection with *Clostridioides difficile* (previously named *Clostridium difficile*) (CDI) causes *Clostridioides difficile*-associated diseases (CDAD). Over 450,000 cases of CDI occur in the US annually, with over 80,000 first recurrences and approximately 29,000 deaths. The most common precipitant is antibiotic use. Antibiotics cause loss of colonization resistance with the potential establishment of a long-lasting, species-poor microbiota susceptible to pathogen invasion. Oral vancomycin and metronidazole treatment are associated with high CDI recurrence rates, likely due to deleterious effects on resident colonic flora. Recurrences are costly in terms of both clinical burden and healthcare resource utilization. In one study, readmission was required in approximately one-third of recurrence cases.

Both microbiota biomass and composition at the intestinal-bacterial interface likely influence the *C. difficile* colonization niche. Although colonization resistance has been associated with specific taxa, it is likely that different, yet diverse, microbiota community structures can confer protection. Consistent characteristics of communities susceptible to CDI are low diversity levels and diminished metabolic function with loss of relative abundance of members of the Bacteroidetes and Firmicutes phyla and increases in that of Proteobacteria. Faecal microbiota transplantation (FMT) normalizes these features and breaks the CDI recurrence cycle.

In aggregate, these data support a role for CDI agents with minimal effects on indigenous microbiota to reduce risk of recurrence.

Ridinilazole (also known as SMT19969, and which may be variously referenced as 2,2'-di(pyridin-4-yl)-1H,1'H-5,5'-bibenzo[d]imidazole or 5,5'-bis[2-(4-pyridinyl)-1H-benzimidazole] in the literature), is a narrow-spectrum, poorly-absorbable, potent *C. difficile*-targeting antimicrobial. Ridinilazole may be represented by the following formula:

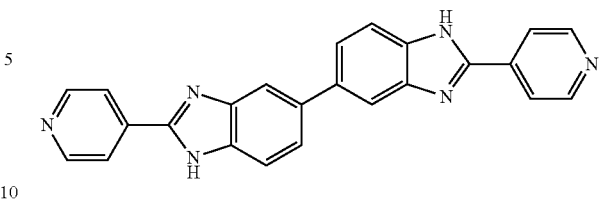

(I)

In a recent Phase 2 randomized, controlled, double-blinded clinical trial comparing its efficacy to vancomycin (Vickers et al. (2017) Lancet Infect Dis 17: 735-744), ridinilazole was associated with marked reduction in rates of recurrent disease (14.3% vs. 34.8%). Ridinilazole exhibits enhanced preservation of the human intestinal microbiota compared to vancomycin (which may contribute to the reduced CDI recurrence observed in the Phase 2 study).

Ridinilazole is a BCS class IV, orally administered and locally acting (lower intestines) GI antibiotic with minimal systemic exposure and very low solubility across physiologically relevant pH. BCS class IV drugs are known to present particular formulation challenges, especially in the case of oral formulations (see e.g. Ghadi and Dand (2017) *BCS class IV drugs: Highly notorious candidates for formulation development* Journal of Controlled Release, 248: 71-95).

Existing clinical ridinilazole formulations include an aqueous suspension used in a Phase 1 study. Individual doses (2 mg-2000 mg) were manufactured at site and dosed within a 24-hour period. The drug substance (2 mg-2000 mg) was suspended in 30 ml water for injection (WFI) with additional WFI provided as rinse. Ahead of preparation of the unit doses the drug substance was de-aggregated in a pestle and mortar for organoleptic reasons. This formulation successfully delivered the powdered drug substance through the gastrointestinal tract to the colon.

In Phase 2 studies, ridinilazole was formulated as an immediate release liquid-filled hard-gelatin capsule at a strength of 200 mg. This dosage form was also capable of readily dispersing within the stomach and delivering the powdered drug substance through the gastrointestinal tract to the colon. The ridinilazole capsules were manufactured by liquid filling of a semi-solid blend of ridinilazole and Vitamin E Polyethylene Glycol Succinate (Vitamin E TPGS). Ahead of filling ridinilazole was evenly dispersed within Vitamin E TPGS through high shear mixing. Vitamin E TPGS was selected based on its ability to efficiently disperse the active ingredient within a volume compatible with the drug loading, unit dose and capsule size, its compatibility with the manufacturing process, and its compatibility with the active ingredient and capsule shell.

However, the suspension and liquid-filled capsule ridinilazole formulations have severe disadvantages. Suspension formulations are inconvenient, as they may need to be extemporaneously prepared immediately prior to use, or if ready prepared may have to be physically processed (e.g. by thorough shaking) before dosing, otherwise there is risk that a non-uniform product is employed when measuring the actual dose to be administered. Indeed, risks arising from lack of uniformity are acute in relation to suspension formulations). For example, the dose must be measured out with a spoon or an oral syringe for administration from the bottle of liquid, which typically leads to inaccuracy of dosing from dose to dose. Moreover, even ready to use suspensions are inconvenient, as the entire course of treatment needs is contained within a bottle of liquid that must be properly handled and stored by the patient.

Liquid-filled capsule formulations also suffer from risks associated with non-uniform doses, since the fluid suspension may suffer sedimentation unless elaborate (and costly) precautions are taken with temperature control and agitation during capsule filling. Capsule filling also requires great care to assure the exact dose of fluid is metered into each capsule, requiring specialist equipment for commercial manufacturing which is not widely available.

A solid tablet oral dosage form of ridinilazole is therefore highly desirable. However, the therapeutic dose of ridinilazole is 200 mg twice a day (BID), with a daily dose of 400 mg. A relatively high drug load is therefore required in any oral tablet appropriately sized for safe and convenient administration with good patient compliance. Consequently, the bulk and surface properties of ridinilazole significantly impact on manufacturability and processability. As a statically charged, micronized material of very low aqueous solubility, poor wettability, low bulk density and poor flow characteristics, the formulation of ridinilazole as appropriately sized solid oral tablets therefore presents acute problems.

The present inventors have now discovered that problems arising from these characteristics can be overcome by selection of a specific particle size of ridinilazole tetrahydrate crystal agglomerates in the context of an intragranular solid phase, which permits, via wet or dry granulation processes, the production of ridinilazole granules with physical attributes (including size, density, morphology and microstructure) which render them unexpectedly useful in the context of solid tablet oral dosage forms.

As a result, tablets including ridinilazole tetrahydrate as an active ingredient, which overcome the problems associated with the existing Phase I and Phase II liquid formulations described above, while exhibiting superior delivery characteristics over the Phase II capsule formulation, can now be provided to further improve the treatment of CDI.

SUMMARY OF THE INVENTION

The invention generally encompasses tablet formulations including
(i) ridinilazole crystal agglomerates; and
(ii) an intragranular solid phase incorporated in an extragranular solid phase,
wherein:
(a) the intragranular phase comprises ridinilazole crystal agglomerates having a particle size $D^{90}$ of less than 30 μm dispersed within a first pharmaceutically acceptable excipient system; and
(b) the extragranular phase comprises a second pharmaceutically acceptable excipient system.

In certain embodiments, the intragranular phase and the extragranular phase are different.

In certain embodiments, the ridinilazole crystal agglomerates comprise ridinilazole tetrahydrate, preferably ridinilazole tetrahydrate crystal agglomerates.

In certain embodiments, the ridinilazole crystal agglomerates has a particle size $D^{90}$ of about 7 to about 25 μm.

In certain embodiments, the ridinilazole crystal agglomerates has a particle size $D^{90}$ of about 10 to about 20 μm.

In certain embodiments, the ridinilazole crystal agglomerates comprises ridinilazole tetrahydrate Form A.

In certain embodiments, the ridinilazole tetrahydrate is present in the tablet in an amount of up to 40%, 45%, 50%, 55%, 60%, 65%, 70%, 75% or 80% wt/wt.

In certain embodiments, the ridinilazole tetrahydrate is present in the tablet at a concentration greater than or equal to about 40% wt/wt.

In certain embodiments, the intragranular phase is present in the tablet at a concentration of about 65 to about 95% wt/wt.

In certain embodiments, the extragranular phase is present in the tablet at a concentration of about 5 to about 35% wt/wt.

In certain embodiments, the first excipient system is present in the tablet at a concentration of up to about 40% wt/wt.

In certain embodiments, the first excipient system comprises a first diluent, and wherein the first diluent is present in the tablet at a concentration of up to 35% wt/wt.

In certain embodiments, the first diluent comprises lactose monohydrate and/or microcrystalline cellulose,
wherein the lactose monohydrate is present in the tablet at a concentration of up to 30% wt/wt, and the microcrystalline cellulose is present in the tablet at a concentration of up to 10% wt/wt.

In certain embodiments, the first excipient system comprises a first disintegrant,
wherein the first disintegrant is selected from croscarmellose sodium, crospovidone, microcrystalline cellulose, polacrilin potassium, powdered cellulose, pregelatinized starch, sodium starch glycolate and starch.

In certain embodiments, the first disintegrant is present in the tablet at a concentration of up to 2% wt/wt.

In certain embodiments, the first excipient system comprises a binder,
wherein the binder is selected from the group consisting of polyvinyl pyrrolidone (PVP), copovidone (PVP-polyvinyl acetate copolymer), partially gelatinized starch (PGS), and cellulose ethers, wherein the cellulose ethers are selected from hydroxypropyl cellulose (HPC), methyl cellulose (MC), hydroxypropylmethyl cellulose (HPMC), ethylcellulose (EC) and sodium carboxymethyl cellulose (NaCMC).

In certain embodiments, the binder is present in the tablet at a concentration of up to 3% wt/wt.

In certain embodiments, the second excipient system is present in the tablet at a concentration of up to 10% wt/wt.

In certain embodiments, the second excipient system comprises a second diluent and/or a second disintegrant and/or a lubricant.

In certain embodiments, the second diluent is present in the tablet at a concentration of up to 6% wt/wt.

In certain embodiments, the second diluent comprises lactose monohydrate and/or microcrystalline cellulose, wherein
the lactose monohydrate is present in the tablet at a concentration of up to 5% wt/wt, and the microcrystalline cellulose is present in the tablet at a concentration of up to 2% wt/wt.

In certain embodiments, the second excipient system comprises a second disintegrant,
wherein the second disintegrant is selected from croscarmellose sodium, crospovidone, microcrystalline cellulose, polacrilin potassium, powdered cellulose, pregelatinized starch, sodium starch glycolate and starch.

In certain embodiments, the second disintegrant is present in the tablet at a concentration of up to 3% wt/wt.

In certain embodiments, the second excipient system comprises a lubricant,
wherein the lubricant is selected from: (a) fatty acids; (b) metallic salts of fatty acids; (c) combinations of fatty acids and metallic salts thereof; (d) fatty acid esters; (e) metallic salts of fatty acid esters; and (f) inorganic materials and polymers.

In certain embodiments, the lubricant comprises:

(i) a fatty acid selected from the group consisting of stearic acid, palmitic acid and myristic acid;

(ii) a metallic salt of a fatty acid selected from magnesium stearate, calcium stearate and zinc stearate;

(iii) a combination of stearic acid and magnesium stearate;

(iv) a fatty acid ester selected from glyceride esters and sugar esters;

(v) a glyceride ester selected from glyceryl monostearate, glyceryl tribehenate, and glyceryl dibehenate;

(vi) a sugar ester selected from sorbitan monostearate and sucrose monopalmitate; and/or (vii) sodium stearyl fumarate or lysine.

or combinations thereof.

In certain embodiments, the lubricant is present in the tablet at a concentration of up to 1% wt/wt.

In certain embodiments, the second excipient system comprises lactose monohydrate, microcrystalline cellulose, croscarmellose sodium and magnesium stearate, and magnesium stearate.

In certain embodiments, the formulation is substantially anhydrous.

In certain embodiments, the tablet contains about 100 about 400 mg of ridinilazole tetrahydrate.

In certain embodiments, the tablet contains about 200 mg of ridinilazole tetrahydrate (which is equivalent to 169 mg of ridinilazole on an anhydrous basis).

In certain embodiments, the tablet formulation comprises or consists of:

| Component | Component Function | Quantity (mg) | % Formula (% w/w) |
|---|---|---|---|
| Intragranular Phase | | | |
| Ridinilazole tetrahydrate Form A | Active | 200.00 | 50.00 |
| Lactose monohydrate 200M | First diluent | 101.96 | 25.49 |
| Microcrystalline Cellulose (Avicel PH101) | First diluent | 38.04 | 9.51 |
| Hydroxypropylcellulose | Binder | 12.00 | 3.00 |
| Croscarmellose sodium | First disintegrant | 8.00 | 2.00 |
| Extragranular Phase | | | |
| Lactose monohydrate 100M | Second diluent | 17.48 | 4.37 |
| Microcrystalline Cellulose (Avicel PH102) | Second diluent | 6.52 | 1.63 |
| Croscarmellose sodium | Second disintegrant | 12.00 | 3.00 |
| Magnesium stearate | Lubricant | 4.00 | 1.00 |
| TOTAL | | 400.00 | 100.00 |
| Coating | | | |
| Opadry II Brown | Film Coat | 12.00 | 3.00 (w/w) |
| TOTAL | | 412.00 | N/A |

In certain embodiments, some or all of the intragranular phase takes the form of inclusions embedded within a matrix formed by the extragranular phase.

In certain embodiments, the tablet formulation exhibits a $T_{MAX}$ of less than 3 hours for ridinilazole tetrahydrate in ileal effluent as measured using the TIM-1 dynamic in vitro gastrointestinal model.

In certain embodiments, the tablet formulation exhibits a $T_{MAX}$ of less than 2 hours for ridinilazole tetrahydrate in ileal effluent as measured using the TIM-1 dynamic in vitro gastrointestinal model.

According to another embodiment of the invention, there is provided a ridinilazole tetrahydrate tablet comprising an intragranular solid phase incorporated in an extragranular solid phase, wherein: (a) the intragranular phase comprises ridinilazole tetrahydrate agglomerates having a particle size $D_{90}$ of about 4 μm to about 30 μm dispersed within a first pharmaceutically acceptable excipient system; and (b) the extragranular phase comprises a second pharmaceutically acceptable excipient system, wherein the first and second excipient systems are different.

In embodiments, the ridinilazole is in the form of ridinilazole tetrahydrate, preferably in the form of ridinilazole tetrahydrate crystal agglomerates, more preferably ridinilazole tetrahydrate Form A (as herein defined).

In embodiments, the ridinilazole tetrahydrate crystal agglomerates may have a particle size $D_{90}$ of about 7 to about 25 μm, and preferably have a particle size $D_{90}$ of about 10 to about 20 μm. In various embodiments, the crystal agglomerates may have a particle size $D_{90}$ of about 5, 6, 7, 8, 9, 10, 11, 12, 13, 14, 15, 16, 17, 18, 19, 20, 21, 22, 23, 24, 25, 26, 27, 28, 29, 30, 40, or about 50 μm. In other embodiments, the crystal agglomerates have a particle size $D_{90}$ that is less than 40 μm.

In embodiments, the ridinilazole tetrahydrate is present at any suitable concentration, for example at a concentration of at least 40%, 41%, 42%, 43%, 44%, 45%, 46%, 47%, 48%, 49%, 50%, 55%, 60%, 65% or 70% wt/wt. Preferably, the ridinilazole is present in the tablet at a concentration of up to 40%, 45%, 50%, 55%, 60%, 65%, 70%, 75% or 80% wt/wt. More preferably, the ridinilazole tetrahydrate is present in the tablet at a concentration greater than or equal to 40% wt/wt, for example at about 50% wt/wt.

In embodiments, the intragranular phase is preferably present in the tablet at a concentration of about 65 to about 95% wt/wt, for example about 90% wt/wt. In embodiments, the extragranular phase is preferably present in the tablet at a concentration of about 5 to about 35% wt/wt, for example about 10% wt/wt.

In embodiments, the first excipient system is preferably present in the tablet at a concentration of up to about 40% wt/wt, for example about 40% wt/wt. In embodiments, the first excipient system preferably does not comprise a lubricant. In embodiments, the first excipient system may comprise a first diluent and/or a first disintegrant and/or a binder.

Preferably, the first excipient system comprises a first diluent or combination of first diluents. Any pharmaceutically acceptable diluent, or combination of diluent, may be used. In embodiments, the first diluent may be present in the tablet at a concentration of up to 35% wt/wt, for example about 35% wt/wt. It may comprise, consist of, or consist essentially of, lactose monohydrate and/or microcrystalline cellulose. Preferably, it consists, or consists essentially of, lactose monohydrate and microcrystalline cellulose, for example lactose monohydrate 200M and Avicel PH101®. In more preferred embodiments, lactose monohydrate is present in the tablet at a concentration of up to 30% wt/wt, for example about 25% wt/wt, and the microcrystalline cellulose is present in the tablet at a concentration of up to 10% wt/wt, for example about 9% wt/wt.

In embodiments, the first excipient system may comprise a first disintegrant or combination of first disintegrants. Any pharmaceutically acceptable disintegrant, or combination of disintegrants, may be used. Suitable disintegrants may be selected from croscarmellose sodium, crospovidone, microcrystalline cellulose, polacrilin potassium, powdered cellulose, pregelatinized starch, sodium starch glycolate and starch. In preferred embodiments, the first disintegrant comprises, consists of, or consists essentially of, croscarmellose sodium, for example Ac Di Sol® or Primellose®. In embodiments, the first disintegrant may be present in the tablet at a concentration of up to 2% wt/wt, for example about 2% wt/wt.

In embodiments, the first excipient system may comprise a binder. Any pharmaceutically acceptable binder, or combination of binders, may be used. Suitable binders may comprise, consist of, or consist essentially of, a hydrophilic polymer. For example, the binder may be selected from polyvinyl pyrrolidone (PVP), copovidone (PVP-polyvinyl acetate copolymer), partially gelatinized starch (PGS), and cellulose ethers. In embodiments, the binder may therefore comprise a cellulose ether selected from hydroxypropyl cellulose (HPC), methyl cellulose (MC), hydroxypropylmethyl cellulose (HPMC), ethylcellulose (EC) and sodium carboxymethyl cellulose (NaCMC). In preferred embodiments, the binder comprises, consists of, or consists essentially of, hydroxypropylcellulose. In embodiments, the binder is preferably present in the tablet at a concentration of up to 3% wt/wt, for example about 3% wt/wt.

Preferably, the first excipient system consists, or consists essentially, of the first diluent, the first disintegrant and the binder. In such embodiments, the first excipient system preferably consists, or consists essentially, of lactose monohydrate, microcrystalline cellulose, hydroxypropylcellulose and croscarmellose sodium, for example lactose monohydrate 200M, Avicel PH101, hydroxypropylcellulose and croscarmellose sodium.

In embodiments, the second excipient system may be present in the tablet at a concentration of up to 10% wt/wt, for example about 10% wt/wt. In embodiments, the second excipient system preferably does not comprise a binder. In embodiments, the second excipient system may comprise a second diluent and/or a second disintegrant and/or a lubricant.

Preferably, the second excipient system comprises a second diluent or combination of second diluents. Any pharmaceutically acceptable diluent, or combination of diluents, may be used. In embodiments, the second diluent may be present in the tablet at a concentration of up to 6% wt/wt, for example about 6% wt/wt. In embodiments, the second diluent preferably comprises, consists of, or consists essentially of, lactose monohydrate and/or microcrystalline cellulose, and more preferably may consist, or consist essentially of, lactose monohydrate 100M and Avicel PH102®. In such embodiments, the lactose monohydrate is preferably present in the tablet at a concentration of up to 5% wt/wt, for example about 4.5% wt/wt, and the microcrystalline cellulose is present in the tablet at a concentration of up to 2% wt/wt, for example about 1.5% wt/wt.

In embodiments, the second excipient system may comprise a second disintegrant. Any pharmaceutically acceptable disintegrant, or combination of disintegrants, may be used as the second disintegrant. In embodiments, the second disintegrant may be selected from croscarmellose sodium, crospovidone, microcrystalline cellulose, polacrilin potassium, powdered cellulose, pregelatinized starch, sodium starch glycolate and starch. It may comprise, consist of, or consist essentially of, croscarmellose sodium, for example Ac Di Sol® or Primellose®. The second disintegrant is preferably present in the tablet at a concentration of up to 3% wt/wt, for example about 3% wt/wt.

In embodiments, the second excipient system may comprise a lubricant. Any pharmaceutically acceptable lubricant, or combination of lubricants, may be used. For example, the lubricant may be selected from: (a) fatty acids; (b) metallic salts of fatty acids; (c) combinations of fatty acids and metallic salts thereof; (d) fatty acid esters; (e) metallic salts of fatty acid esters; and (f) inorganic materials and polymers. For example, the lubricant may comprise a fatty acid selected from: stearic acid, palmitic acid and myristic acid. The lubricant may comprise a metallic salt of a fatty acid selected from magnesium stearate, calcium stearate and zinc stearate. Other suitable lubricants comprise combinations of stearic acid and magnesium stearate. The lubricant may also comprise a fatty acid ester selected from glyceride esters and sugar esters. For example, the lubricant may comprise a glyceride ester selected from glyceryl monostearate, glyceryl tribehenate and glyceryl dibehenate. Other suitable lubricants comprise sugar esters selected from sorbitan monostearate and sucrose monopalmitate. The lubricant may also comprise sodium stearyl fumarate or lysine. In preferred embodiments, the lubricant comprises, consists of, or consists essentially of, magnesium stearate. The lubricant is preferably present at a concentration of up to 1% wt/wt, for example about 1% wt/wt.

Preferably, the second excipient system consists, or consists essentially, of the second diluent, the second disintegrant and the lubricant. In such embodiments, the second excipient system preferably consists, or consists essentially, of lactose monohydrate, microcrystalline cellulose, croscarmellose sodium and magnesium stearate, for example lactose monohydrate 100M, Avicel PH102® and magnesium stearate.

In embodiments, the tablet of the invention is preferably dried or substantially anhydrous, for example having a water content of less than 10%, 9.5%, 9%, 8.5%, 8%, 7.5%, 7%, 5%, 4%, 3%, 2% or 1% by weight.

In embodiments, the tablets of the invention contain ridinilazole tetrahydrate in a quantity sufficient to provide a therapeutic effect in a human subject. Preferred are tablets containing about 100 to about 400 mg of ridinilazole tetrahydrate, preferably about 200 mg of ridinilazole tetrahydrate [which is equivalent to 169 mg of anhydrous ridinilazole].

Some or all of the intragranular phase may take the form of inclusions embedded within a matrix formed by the extragranular phase.

In embodiments, the tablet of the invention preferably exhibits a $T_{MAX}$ of less than 3 hours for ridinilazole in ileal effluent as measured using the TIM-1 dynamic in vitro gastrointestinal model as described herein (and known to those skilled in the art). More preferably, the tablet of the invention exhibits a $T_{MAX}$ of less than 2 hours for ridinilazole in ileal effluent as measured using the TIM-1 dynamic in vitro gastrointestinal model. Most preferably, the tablet of the invention exhibits a $T_{MAX}$ of about 1 about 2 hours for ridinilazole in ileal effluent as measured using the TIM-1 dynamic in vitro gastrointestinal model.

In embodiments, the tablet of the invention preferably further comprises a coating. Any suitable coating may be employed, preferred coatings providing protection from contamination, improved stability, organoleptic properties and swallowability. Preferred coatings include pharmaceutically acceptable water-soluble polymer films.

In another aspect of the invention, there is provided a composition comprising granules containing ridinilazole tetrahydrate, optionally in the form of agglomerates, having a particle size $D_{90}$ of about 4 to about 30 µm dispersed within a first pharmaceutically acceptable excipient system, and an extragranular second pharmaceutically acceptable excipient system, wherein the first and second excipient systems are different. The granules may be dispersed, preferably homogeneously, within the second pharmaceutically acceptable excipient system.

The composition of this embodiment is preferably a tableting composition suitable for compression into tablets. Alternatively, or in addition, the composition of this aspect of the invention may be suitable for other uses. Such uses include processes for the formulation of oral and non-oral ridinilazole pharmaceutical compositions of any kind. For example, the compositions of the second aspect of the invention may take the form of, or find application in the preparation of, pharmaceutical formulations other than tablets, including liquid suspensions, granule-filled capsules and granule-filled sachets (or other containers).

In embodiments, the ridinilazole tetrahydrate agglomerates are preferably in the form of ridinilazole tetrahydrate crystal agglomerates, more preferably ridinilazole tetrahydrate Form A (as herein defined).

In embodiments, the granules may be dispersed within the second pharmaceutically acceptable excipient system. Preferably, the granules are homogeneously dispersed within the second pharmaceutically acceptable excipient system. The granules are dried, for example having a water content of less than 10%, 5%, 2% or 1% by weight.

In embodiments, the second pharmaceutically acceptable excipient system may be particulate, and may also be dried, for example having a water content of less than 10%, 9.5%, 9%, 8.5%, 8%, 7.5%, 7%, 5%, 4%, 3%, 2% or 1% by weight.

In embodiments, the crystal agglomerates may have a particle size $D_{90}$ of about 5 µm to about 40 µm, and preferably have a particle size $D_{90}$ of about 10 to about 20 µm. In other embodiments, the crystal agglomerates may have a particle size $D_{90}$ of less than 40 µm, less than 35 µm, less than 30 µm, less than 25 µm, less than 20 µm, less than 15 µm, less than 10 µm, or less than 5 µm.

In embodiments, the ridinilazole tetrahydrate may be present in the composition at a concentration of at least 40%, 41%, 42%, 43%, 44%, 45%, 46%, 47%, 48%, 49%, 50%, 55%, 60%, 65% or 70% wt/wt, preferably at a concentration of up to 40%, 45%, 50%, 55%, 60%, 65%, 70%, 75% or 80% wt/wt, more preferably at a concentration ≥40% wt/wt, for example at about 50% wt/wt.

In embodiments, the granules may be present in the composition at a concentration of 65-95% wt/wt, preferably at about 90% wt/wt.

In embodiments, the second excipient system may be present in the composition at a concentration of about 5 to about 35% wt/wt, preferably at about 10% wt/wt.

In embodiments, the first and second excipient systems are preferably as defined above in relation to the tablets of the invention.

In embodiments, the tableting composition is preferably dried, for example having a water content of less than 10%, 9.5%, 9%, 8.5%, 8%, 7.5%, 7%, 5%, 4%, 3%, 2% or 1% by weight.

Most preferred are tableting compositions which are suitable for compression into a tablet of the invention as defined according to the first aspect of the invention above.

In another aspect of the invention, there is provided a process for producing a granular ridinilazole tetrahydrate composition comprising the steps of:
(a) providing ridinilazole tetrahydrate agglomerates having a particle size $D_{90}$ of about 4 to about 30 µm;
(b) mixing the agglomerates of step (a) with a first pharmaceutically acceptable intragranular excipient system to form a pre-granulation mix;
(c) granulating the pre-granulation mix to form granules containing said crystal agglomerates dispersed within said first pharmaceutically acceptable excipient system; and
(d) blending the granules of step (c) with a second pharmaceutically acceptable extragranular excipient system to form a granular ridinilazole composition, optionally suitable for compression into a tablet.

In embodiments, the process is preferably suitable for producing a granular ridinilazole composition as defined according to the second aspect of the invention above. The granular ridinilazole tetrahydrate composition of step (d) is preferably suitable for compression into a tablet as defined according to the first aspect of the invention above. Alternatively, or in addition, the granular ridinilazole tetrahydrate composition of step (d) may also be suitable for other uses, including processes for the formulation of oral and non-oral ridinilazole tetrahydrate pharmaceutical compositions of any kind. For example, the ridinilazole tetrahydrate composition of step (d) may take the form of, or find application in the preparation of, pharmaceutical formulations other than tablets, including liquid suspensions, granule-filled capsules and granule-filled sachets (or other containers).

In embodiments, the ridinilazole tetrahydrate agglomerates are preferably in the form of ridinilazole tetrahydrate crystal agglomerates, more preferably ridinilazole tetrahydrate Form A (as herein defined). The crystal agglomerates may have a particle size $D_{90}$ of about 7 to about 25 µm, and preferably have a particle size $D_{90}$ of about 10 to about 20 µm.

In embodiments, the ridinilazole tetrahydrate may be present in the granules at a concentration of at least 40%, 41%, 42%, 43%, 44%, 45%, 46%, 47%, 48%, 49%, 50%, 55%, 60%, 65% or 70% wt/wt, for example at a concentration of up to 40%, 45%, 50%, 55%, 60%, 65%, 70%, 75% or 80% wt/wt. Preferably, the ridinilazole tetrahydrate is present in the granules at a concentration ≥40% wt/wt, for example at about 50% wt/wt.

In embodiments, the granules are preferably present in the granular ridinilazole tetrahydrate composition of step (d) at a concentration of about 65 to about 95% wt/wt, for example about 90% wt/wt.

In embodiments, the second excipient system may be present in the granular ridinilazole composition of step (d) at a concentration of about 5 to about 35% wt/wt, for example about 10% wt/wt.

In embodiments, the first and second excipient systems are preferably as defined above in relation to the tablets and tableting compositions of the invention.

In embodiments, the providing step (a) preferably comprises reducing the particle size of crystalline ridinilazole, for example by micronization and/or by a process comprising the steps of milling, grinding, sieving and/or screening, e.g. by air jet milling.

In embodiments, the mixing step (b) may further comprise the step of screening or sieving the first excipient system prior to mixing with the agglomerates.

In some embodiments, the mixing step (b) comprises the steps of:

(b1) mixing the agglomerates of step (a) with an initial fraction of a first pharmaceutically acceptable intragranular excipient system to form an initial pre-granulation mix;

(b2) passing the pre-granulation mix of step (b1) through a screen or sieve to form a screened initial pre-granulation mix; and (b3) passing a second fraction of a first pharmaceutically acceptable intragranular excipient system through the screen or sieve of step (b2) to form a screened second fraction; and then (b4) mixing the screened initial pre-granulation mix of step (b2) with the screened second excipient fraction of step (b3) to form a final pre-granulation mix for granulation according to step (c).

In the above embodiments, the initial fraction of a first pharmaceutically acceptable intragranular excipient system may be a subset of the constituent excipients of a first excipient system as herein described. For example, the initial fraction may constitute all of the constituent excipients of a first excipient system as herein described except for some or all of the first diluent (for example, the microcrystalline cellulose first diluent of the preferred embodiments described above).

Also in the above embodiments, the agglomerates of step (a) may comprise re-agglomerated ridinilazole tetrahydrate particles. In such cases, steps (b1) and (b2) break down and remove the re-agglomerated ridinilazole particles such that the screened initial pre-granulation mix of step (b2) contains uniformly distributed ridinilazole tetrahydrate crystal agglomerates.

The particle size of the API can be analysed by any convenient method, including sedimentation field flow fractionation, photon correlation spectroscopy, light scattering (e.g. laser diffraction) and disk centrifugation. Preferred is dry laser diffraction as described herein.

The mixing step (b) preferably comprises high shear dry blending.

The granulation step (c) may comprise dry granulation. However, the granulation step (c) preferably comprises wet granulation, more preferably high-shear wet granulation.

In a fourth aspect of the invention, there is provided a process for making a ridinilazole tetrahydrate tablet comprising the steps of:

(a) providing a granular ridinilazole composition by a process of the third aspect of the invention; and then (b) compressing the granular composition to produce the ridinilazole tablet.

In embodiments, the tableting process may further comprise the step of coating said ridinilazole tablet to form a coated ridinilazole tetrahydrate tablet. It may also further comprise the step of packaging a plurality of the ridinilazole tablets to form a ridinilazole patient pack, or a bottle or other container containing sufficient tablets for a single course of treatment (e.g., about 20 tablets).

In a fifth aspect of the invention, there is provided a granular ridinilazole tetrahydrate composition suitable for compression into tablets obtainable by the process of the third aspect of the invention.

In another aspect of the invention, there is provided a ridinilazole tetrahydrate tablet, patient pack or container obtainable by the process of the fourth aspect of the invention.

In another aspect of the invention, there is provided a tablet of the invention for use in the treatment, therapy or prophylaxis of CDI or CDAD.

In another aspect of the invention, there is provided the use of the tablet of the invention for the manufacture of a medicament for use in the treatment, therapy or prophylaxis of CDI or CDAD.

In another aspect of the invention, there is provided a method for the treatment, therapy or prophylaxis of CDI or CDAD in a patient in need thereof, comprising orally administering to the patient a tablet of the invention.

In another embodiment of the invention, there is provided a tablet formulation comprising (i) ridinilazole tetrahydrate; and (ii) an intragranular solid phase incorporated in an extragranular solid phase, wherein:

(a) the intragranular phase comprises ridinilazole crystal agglomerates having a particle size $D_{90}$ of about 4 to about 30 µm dispersed within a first pharmaceutically acceptable excipient system; and (b) the extragranular phase comprises a second pharmaceutically acceptable excipient system, wherein the first and second excipient systems are different, and wherein the ridinilazole tetrahydrate crystal agglomerates have a particle size $D_{90}$ of about 7 to about 25 µm.

In embodiments, the crystal agglomerates may have a particle size $D_{90}$ of about 5 µm to about 40 µm, and preferably have a particle size $D_{90}$ of about 10 to about 20 µm. In other embodiments, the crystal agglomerates may have a particle size $D_{90}$ of less than 40 µm, less than 35 µm, less than 30 µm, less than 25 µm, less than 20 µm, less than 15 µm, less than 10 µm, or less than 5 µm.

In embodiments, the ridinilazole crystal agglomerates comprise ridinilazole tetrahydrate.

In embodiments, the ridinilazole tetrahydrate crystal agglomerates comprise ridinilazole tetrahydrate Form A.

In embodiments, the ridinilazole is present in the tablet at an amount of up to 40%, 45%, 50%, 55%, 60%, 65%, 70%, 75% or 80% wt/wt.

In embodiments, the ridinilazole is present in the tablet at a concentration ≥40% wt/wt, for example at about 50% wt/wt.

In embodiments, the intragranular phase is present in the tablet at a concentration of about 65 to about 95% wt/wt, for example about 90% wt/wt.

In embodiments, the extragranular phase is present in the tablet at a concentration of about 5 to about 35% wt/wt, for example about 10% wt/wt.

In embodiments, the first excipient system is present in the tablet at a concentration of up to 40% wt/wt, for example about 40% wt/wt.

In embodiments, the first excipient system comprises a first diluent, and wherein the first diluent is present in the tablet at a concentration of up to 35% wt/wt.

In embodiments, the first diluent comprises, consists of, or consists essentially of, lactose monohydrate and/or microcrystalline cellulose, and wherein the lactose monohydrate is present in the tablet at a concentration of up to 30% wt/wt, and the microcrystalline cellulose is present in the tablet at a concentration of up to 10% wt/wt.

In embodiments, the first excipient system comprises a first disintegrant, wherein the first disintegrant is selected from croscarmellose sodium, crospovidone, microcrystalline cellulose, polacrilin potassium, powdered cellulose, pregelatinized starch, sodium starch glycolate and starch.

In embodiments, the first disintegrant is present in the tablet at a concentration of up to 2% wt/wt, for example about 2% wt/wt.

In embodiments, the first excipient system comprises a binder, wherein the binder is selected from polyvinyl pyrrolidone (PVP), copovidone (PVP-polyvinyl acetate copolymer), partially gelatinized starch (PGS), and cellulose ethers, wherein the cellulose ethers are selected from hydroxypropyl cellulose (HPC), methyl cellulose (MC), hydroxypropylmethyl cellulose (HPMC), ethylcellulose (EC) and sodium carboxymethyl cellulose (NaCMC).

In embodiments, the binder is present in the tablet at a concentration of up to 3% wt/wt, for example about 3% wt/wt.

In embodiments, the second excipient system is present in the tablet at a concentration of up to 10% wt/wt, for example about 10% wt/wt.

In embodiments, the second excipient system comprises a second diluent and/or a second disintegrant and/or a lubricant.

In embodiments, the second diluent is present in the tablet at a concentration of up to 6% wt/wt.

In embodiments, the second diluent comprises lactose monohydrate and/or microcrystalline cellulose, wherein the lactose monohydrate is present in the tablet at a concentration of up to 5% wt/wt, and the microcrystalline cellulose is present in the tablet at a concentration of up to 2% wt/wt.

In embodiments, the second excipient system comprises a second disintegrant, optionally wherein the second disintegrant is selected from croscarmellose sodium, crospovidone, microcrystalline cellulose, polacrilin potassium, powdered cellulose, pregelatinized starch, sodium starch glycolate and starch.

In embodiments, the second disintegrant is present in the tablet at a concentration of up to 3% wt/wt, for example about 3% wt/wt.

In embodiments, the second excipient system comprises a lubricant, wherein the lubricant is selected from: (a) fatty acids; (b) metallic salts of fatty acids; (c) combinations of fatty acids and metallic salts thereof; (d) fatty acid esters; (e) metallic salts of fatty acid esters; and (f) inorganic materials and polymers.

In embodiments, the lubricant comprises a fatty acid selected from: stearic acid, palmitic acid and myristic acid; a metallic salt of a fatty acid selected from magnesium stearate, calcium stearate and zinc stearate; a combination of stearic acid and magnesium stearate; a fatty acid ester selected from glyceride esters and sugar esters; a glyceride ester selected from glyceryl monostearate, glyceryl tribehenate, and glyceryl dibehenate, a sugar ester selected from sorbitan monostearate and sucrose monopalmitate; sodium stearyl fumarate or lysine.

In embodiments, the lubricant is present in the tablet at a concentration of up to 1% wt/wt.

In embodiments, the second excipient system comprises lactose monohydrate, microcrystalline cellulose, croscarmellose sodium and magnesium stearate, for example lactose monohydrate 100M, Avicel PH102® and magnesium stearate.

In embodiments, the tablet contains about 100 about 400 mg of ridinilazole tetrahydrate.

In embodiments, the tablet contains about 200 mg of ridinilazole tetrahydrate.

In embodiments, some or all of the intragranular phase takes the form of inclusions embedded within a matrix formed by the extragranular phase.

In embodiments, the tablet formulation exhibits a $T_{MAX}$ of less than 3 hours for ridinilazole in ileal effluent as measured using the TIM-1 dynamic in vitro gastrointestinal model.

In embodiments, the tablet formulation exhibits a $T_{MAX}$ of less than 2 hours for ridinilazole in ileal effluent as measured using the TIM-1 dynamic in vitro gastrointestinal model.

BRIEF DESCRIPTION OF THE FIGURES

FIG. 15 shows the Bristol Stool Chart and various types of fecal morphology.

FIG. 19 illustrates an exemplary manufacturing process for the tablets of the invention.

DETAILED DESCRIPTION

Figure 1:
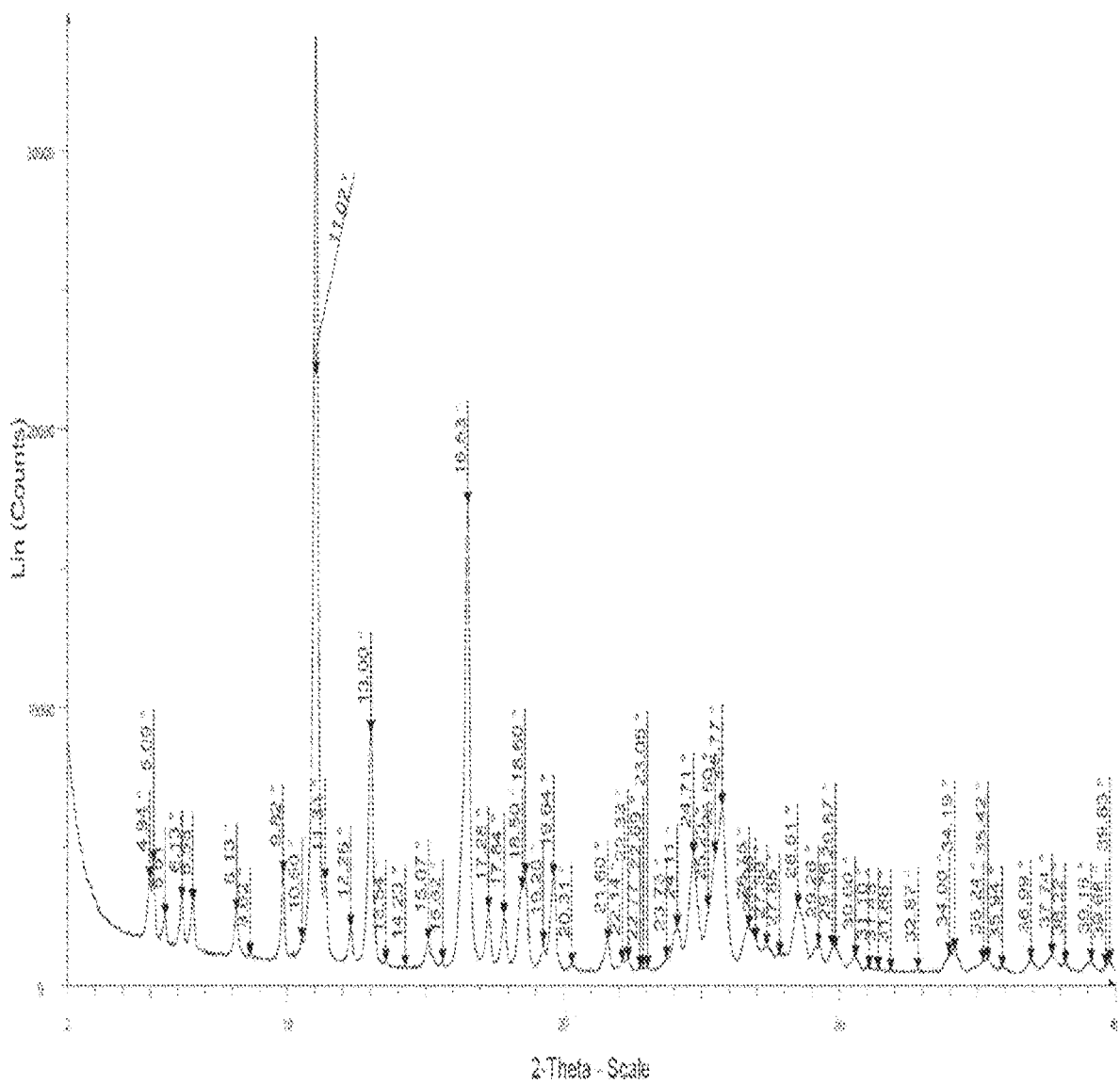
FIG. 1 shows a representative x-ray powder diffraction pattern for ridinilazole tetrahydrate Form A.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art.

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "about" is used in relation to a numerical value or range is to be interpreted as being as accurate as the method used to measure it. The term may also be used in this context synonymously with the term "or thereabout", so that references to "about" in relation to a particular numerical value or range may also be interpreted to define that particular numerical value or range or thereabout. Thus, a reference to "about x" may be interpreted as "x, or about x", while a reference to "about x to y" may be interpreted as "x to y, or about x to about y, or about x to y". The term may also be interpreted to define an error margin of ±10% in relation to the referenced numerical value or to the upper and lower limits of the referenced range. In certain embodiments, the term "about" when referring to a value includes the stated value +/−10% of the stated value. For example, about 50% includes a range of from 45% to 55%, while about 20 molar equivalents includes a range of from 18 to 22 molar equivalents. Accordingly, when referring to a range, "about" refers to each of the stated values +/−10% of the stated value of each end of the range.

The term "administering" refers to administration of the composition of the present invention to a subject.

The term "aggregates" refers to two or more primary particles tightly bound together by rigid chemical bonding resulting from sintering or cementation. Primary particles are inorganic or organic structures held together by atomic or molecular bonding. They are the "fundamental" particles. Primary particles cannot be separated into smaller particles except by the application of ultrahigh energy. In any sample they are usually present at only a fraction of a percent. Aggregation is the coalescence of particles by processes other than heat/pressure, i.e., precipitation of ionic salts onto surfaces during manufacture. Aggregates are typically formed when powders are heated, compressed, or dried from a suspension. They have a large interfacial area of contact between each particle and the force necessary to rupture these bonds is considerable. Aggregates constitute, for all practical purposes, the largest single fraction of any particle size distribution (PSD) that one can hope to achieve in a formulation.

The term "agglomerates" refers to collections of aggregates, loosely held together at point-to-point contact by weak electromagnetic forces, van der Waals forces, mechanical friction, and interlocking. Agglomerates are formed when fine particles are handled, shaken, rolled or stored undisturbed in a single position. They can readily be broken apart with proper dispersion techniques.

The term bioisostere (or simply isostere) is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see article by Tacke and Zilch in Endeavour, New Series, 1986, 10 191-197). The sila-substituted isosteres (silicon isosteres) may exhibit improved pharmacological properties, and may for example be better tolerated, have a longer half-life or exhibit increased potency (see for example article by Englebienne in Med. Chem., 2005, 1(3), 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon bioisosteres) of the compounds of the invention.

The term "composition" as used herein is intended to encompass a product that includes the specified active product ingredient (API) (e.g., ridinilazole tetrahydrate, preferably in Form A) and pharmaceutically acceptable excipients, carriers or diluents as described herein, such as in specified amounts defined throughout the originally filed disclosure, which results from combination of specific components, such as specified ingredients in the specified amounts as described herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

The term "disintegrant" refers to a pharmaceutical excipient that is incorporated into a composition to promote their disintegration when they come into contact with a liquid. For example, a disintegrant is a pharmaceutically acceptable agent, used in preparation of tablets, which causes tablets to disintegrate and release medicinal substances on contact with moisture. Examples of disintegrants include, without limitation, crosslinked polymers, including crosslinked polyvinylpyrrolidone (crospovidone), crosslinked sodium carboxymethyl cellulose (croscarmellose sodium), and modified starch sodium starch glycolate and the like.

As used herein, the term "$D^{\#}$" means distribution particle size distribution. For example, the unit, $D^{10}$ represents the 10% of particles in the powders are smaller than this size. Typically, the unit is μm. A laser particle size analyzer measures the particle using laser with different angles, and then retrieves the diffraction patterns from the image sensors. And finally, by performing addition, subtraction, or cross analysis calculations, the instrument determines the statistical proportion of the sizes of particles. $D^{90}$ means that 90% of the total particles are smaller than this size. For example, $D^{10}$ is 2.557 μm, and $D^{90}$ is 46.88 μm. The two sizes, $D^{10}$ and $D^{90}$, enclose the range of particle sizes of the sample powders. The particle size exceeding this range can be ignored, because of the small number of particles. $D^{50}$ means that 50% of the total particles are smaller than this size, or 50% of the particles are larger than this size. $D^{50}$ is the median particle size distribution, we can call this value, Median.

As used herein, the term "disposed over" refers to the placement of one phase or coating on top of another phase or coating. Such placement can conform to the shape of the underlying phase or coating such that the layering of phases and coatings do not leave substantial gaps there between.

As used herein, the term "extragranular phase" refers to the bulk portion of a core structure that resides between the internal phase and the outer layer coatings of a composition. While the extragranular phase could itself be considered a coating, it can be generally thicker than a mere coating, thereby imparting significant structure/dimensions to the composition.

As used herein, the term "Form A" of ridinilazole refers to the crystalline form of ridinilazole tetrahydrate characterized by a powder X-ray diffractogram comprising characteristic peaks at 2-Theta angles of (11.02±0.2°), (16.53±0.2°) and (13.0±0.2°).

As used herein, the term "Form D" of ridinilazole refers to the crystalline form of ridinilazole anhydrate characterized by a powder X-ray diffractogram comprising characteristic peaks at 2-Theta angles of (12.7±0.2°), (23.18±0.2°) and (27.82±0.2°), optionally comprising characteristic peaks at 2-Theta angles of (12.7±0.2°), (23.18±0.2°), (27.82±0.2°), (19.5±0.2°) and (22.22±0.2°).

As used herein, the term "Form N" of ridinilazole refers to the crystalline form of ridinilazole tetrahydrate characterized by a powder X-ray diffractogram comprising characteristic peaks at 2-Theta angles of (10.82±0.2°), (13.35±0.2°) and (19.15±0.2°), optionally comprising characteristic peaks at 2-Theta angles of (10.82±0.2°), (13.35±0.2°), (19.15±0.2°), (8.15±0.2°) and (21.74±0.2)°

One of ordinary skill in the art will appreciate that an XRPD pattern may be obtained with a measurement error that is dependent upon the measurement conditions employed. In particular, it is generally known that intensities in an XRPD pattern may fluctuate depending upon measurement conditions employed. Relative intensities may also vary depending upon experimental conditions and so relative intensities should not be considered to be definitive. Additionally, a measurement error of diffraction angle for a conventional XRPD pattern is typically about 5% or less, and such degree of measurement error should be taken into account when considering stated diffraction angles. It will be appreciated that the various crystalline forms described herein are not limited to the crystalline forms that yield X-ray diffraction patterns completely identical to the X-ray diffraction patterns depicted in the accompanying Figures. Rather, crystalline forms of ridinilazole that provide X-ray diffraction patterns substantially in accordance (as hereinbefore defined) with those shown in the Figures fall within the scope of the present invention.

The term "glidant" refers to a substance that is added to a powder to improve its flowability and/or lubricity. Examples of glidants, may include, but is not limited to, magnesium stearate, fumed silica, starch and talc and the like.

The term "granulated mixture" refers to a mixture of two or more agents made by mixing the two or more agents and granulating them together in a particulate form. Such a mixture provides particulate material that is composed of two or more agents.

The term "hydrophilic silica" refers to a pharmaceutical excipient that can be employed as flow agent (anti-caking), adsorbent and desiccant in solid product forms. It can also be used to increase the mechanical stability and the disintegration rate of the compositions. The hydrophilic silica can be fumed, i.e., referring to its production through a pyrogenic process to generate fine particles of silica. Particles of fumed silica can vary in size such as from 5 nm to 100 nm, or from 5 to 50 nm. The particles can be non-porous and have a surface area from 50-1,000 $m^2/g$ or from 50-600 $m^2/g$. Examples of hydrophilic silicas include Aerosil 200, having a specific surface area of about 200 $m^2/g$.

The term "intragranular phase" refers to the central-most portion of a composition. In the present aspects, the intragranular phase is the location where the active ingredient, ridinilazole tetrahydrate, resides.

The term "lubricant" refers to a substance added to a formulation to reduce friction. Compounds that serve as lubricants can also have properties as glidants. Examples of lubricants may include, but is not limited to, talc, silica, and fats such as vegetable stearin, magnesium stearate or stearic acid and the like.

The term "microcrystalline cellulose," or "MCC," refers to a pharmaceutical grade of cellulose manufactured from a refined wood pulp. The MCC can be unmodified or chemically modified, such as silicified microcrystalline cellulose (SMCC). MCC can serve the function of a bulking agent and aid in tablet formation due to its favorable compressibility characteristics.

The term "patient" or "subject" are used interchangeably refers to a living organism, which includes, but is not limited to a human subject suffering from or prone to a disease or condition that can be treated by administration of a pharmaceutical composition as provided herein. Further non-limiting examples may include, but is not limited to humans, other mammals, bovines, rats, mice, dogs, monkeys, goat, sheep, cows, deer, horse, and other mammalian animals and the like. In some aspects, the patient is human.

As used herein, the term "pharmaceutical pack" defines an array of one or more ridinilazole tetrahydrate tablets, optionally contained within common outer packaging. The tablets may be contained within a blister pack. The pharmaceutical pack may optionally further comprise instructions for use. The compositions of ridinilazole tetrahydrate tablets of the invention may be comprised in a pharmaceutical pack or patient pack.

As used herein, the term "patient pack" defines a package, prescribed to a patient, which contains pharmaceutical compositions for the whole course of treatment. Patient packs usually contain one or more blister pack(s), but may also take the form of a conveniently small bottle or other container containing sufficient tablets for one or more courses of treatment. For example, the container may contain about 20-60 tablets, e.g. about 20 or about 60 tablets (the former being particularly suitable for a single course of treatment, while the latter is particularly suitable for multiple courses of treatment). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The term pharmaceutically acceptable derivative as applied to ridinilazole tetrahydrate define compounds which are obtained (or obtainable) by chemical derivatization of ridinilazole tetrahydrate. The pharmaceutically acceptable derivatives are therefore suitable for administration to or use in contact with mammalian tissues without undue toxicity, irritation or allergic response (i.e. commensurate with a reasonable benefit/risk ratio). Preferred derivatives are those obtained (or obtainable) by alkylation, esterification or acylation of ridinilazole tetrahydrate. The derivatives may be active per se, or may be inactive until processed in vivo. In the latter case, the derivatives of the invention act as prodrugs. Particularly preferred prodrugs are ester derivatives which are esterified at one or more of the free hydroxyls and which are activated by hydrolysis in vivo. Other preferred prodrugs are covalently bonded compounds which release the active parent drug according to formula (I) after cleavage of the covalent bond(s) in vivo.

The pharmaceutically acceptable derivatives of the invention retain some or all of the activity of the parent compound. In some cases, the activity is increased by derivatization. Derivatization may also augment other biological activities of the compound, for example bioavailability.

The term pharmaceutically acceptable salt as applied to ridinilazole tetrahydrate defines any non-toxic organic or inorganic acid addition salt of the free base compound which is suitable for use in contact with mammalian tissues without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenyl acetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). The compounds of the invention may be converted into (mono- or di-) salts by reaction with a suitable base, for example an alkali metal hydroxide, methoxide, ethoxide or tert-butoxide, or an alkyl lithium, for example selected from NaOH, NaOMe, KOH, KOtBu, LiOH and BuLi, and pharmaceutically acceptable salts of ridinilazole tetrahydrate may also be prepared in this way.

These salts and the free base compounds can exist in either a solvated, hydrated or a substantially anhydrous form. Crystalline forms of the compounds of the invention are also contemplated and in general the acid addition salts of the compounds of the invention are crystalline materials.

The term pharmaceutically acceptable solvate as applied to ridinilazole tetrahydrate defines any pharmaceutically acceptable solvate form of a specified compound that retains the biological effectiveness of such compound. Examples of solvates include compounds of the invention in combination with water (hydrates), short-chain alcohols (including isopropanol, ethanol and methanol), dimethyl sulfoxide, ethyl acetate, acetic acid, ethanolamine, acetone, dimethylformamide (DMF), dimethylacetamide (DMAc), pyrrolidones (such as N-Methyl-2-pyrrolidone (NMP)), tetrahydrofuran (THF), and ethers (such as tertiarybutylmethylether (TBME)).

Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulae include compounds having the indicated structure, including the hydrated as well as the non-hydrated forms.

The term pharmaceutically acceptable prodrug as applied to ridinilazole tetrahydrate defines any pharmaceutically acceptable compound that may be converted under physiological conditions or by solvolysis to ridinilazole tetrahydrate in vivo, to a pharmaceutically acceptable salt of such compound or to a compound that shares at least some of the antibacterial activity of the specified compound (e.g. exhibiting activity against *Clostridioides difficile*).

The term pharmaceutically acceptable metabolite as applied to ridinilazole tetrahydrate defines a pharmacologically active product produced through metabolism in the body of ridinilazole tetrahydrate or salt thereof.

Prodrugs and active metabolites of the compounds of the invention may be identified using routine techniques known in the art (see for example, Bertolini et al., J. Med. Chem., 1997, 40, 2011-2016).

The term pharmaceutically acceptable complex as applied to ridinilazole tetrahydrate defines compounds or compositions in which the compound of the invention forms a component part. Thus, the complexes of the invention include derivatives in which the compound of the invention is physically associated (e.g. by covalent or non-covalent bonding) to another moiety or moieties. The term therefore includes multimeric forms of the compounds of the invention. Such multimers may be generated by linking or placing multiple copies of a compound of the invention in close proximity to each other (e.g. via a scaffolding or carrier moiety). The term also includes cyclodextrin complexes.

In its broadest aspect, the present invention contemplates all tautomeric forms, optical isomers, racemic forms and diastereoisomers of the compounds described herein. Those skilled in the art will appreciate that, owing to the asymmetrically substituted carbon atoms present in the compounds of the invention, the compounds may be produced in optically active and racemic forms. If a chiral centre or another form of isomeric centre is present in a compound of the present invention, all forms of such isomer or isomers, including enantiomers and diastereoisomers, are intended to be covered herein. Compounds of the invention containing a chiral centre (or multiple chiral centres) may be used as a racemic mixture, an enantiomerically enriched mixture, or the racemic mixture may be separated using well-known techniques and an individual enantiomer may be used alone. Thus, references to the compounds of the present invention encompass the products as a mixture of diastereoisomers, as individual diastereoisomers, as a mixture of enantiomers as well as in the form of individual enantiomers.

Therefore, the present invention contemplates all optical isomers and racemic forms thereof of the compounds of the invention, and unless indicated otherwise (e.g. by use of dash-wedge structural formulae) the compounds shown herein are intended to encompass all possible optical isomers of the compounds so depicted. In cases where the stereochemical form of the compound is important for pharmaceutical utility, the invention contemplates use of an isolated eutomer.

As used herein, the term "ridinilazole" is used to define the active ingredient in the instant formulations, which is the compound 2,2'-di(pyridin-4-yl)-1H,1'H-5,5'-bibenzo[d]imidazole (which may also be known as 2,2'-di-4-pyridinyl-6,6'-bi-1H-benzimidazole; 5,5'-bis[2-(4-pyridinyl)-1H-benzimidazole]; 2,2'-bis(4-pyridyl)-3H,3'H-5,5'-bibenzimidazole; or 2-pyridin-4-yl-6-(2-pyridin-4-yl-3H-benzimidazol-5-yl)-1H-benzimidazole). The term also includes pharmaceutically acceptable derivatives, salts, hydrates, solvates, complexes, bioisosteres, metabolites or prodrugs of ridinilazole, as herein defined. Ridinilazole tetrahydrate, which is the active ingredient (i.e., Form A) in the drug product has the following structure:

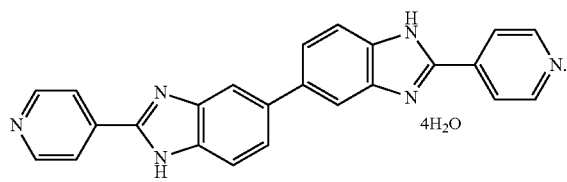

Chemical Formula: C$_{24}$H$_{24}$N$_6$O$_4$
Molecular Weight: 460.49

The abbreviation "XRPD" stands for X-ray powder diffraction (or when context permits, an X-ray powder diffractogram).

"Silicified microcrystalline cellulose," or "SMCC," refers to a particulate agglomerate of coprocessed microcrystalline cellulose and silicon dioxide. Suitable for use in the present invention, SMCC may include amounts from about 0.1% to about 20% silicon dioxide, by weight of the microcrystalline cellulose, where the silicon dioxide can have a particle size from about 1 nanometer (nm) to about 100 microns (μm), based on average primary particle size. For example, the silicon dioxide can contain from about 0.5% to about 10% of the silicified microcrystalline cellulose, or from about 1.25% to about 5% by weight relative to the microcrystalline cellulose. Moreover, the silicon dioxide can have a particle size from about 5 nm to about 40 μm, or from about 5 nm to about 50 μm. The silicon dioxide can have a surface area from about 10 m$^2$/g to about 500 m$^2$/g, or from about 50 m$^2$/g to about 500 m$^2$/g, or from about 175 m$^2$/g to about 350 m$^2$/g. Silicified microcrystalline cellulose is commercially available from a number of suppliers known to one of skill in the art, including Penwest Pharmaceuticals, Inc., under the trademark PROSOLV®. PROSOLV® is available in a number of grades, including, for example, PROSOLV® SMCC 50, PROSOLV® SMCC 90, and PROSOLV® HD. Other products include, without limitation, SMCC 50LD, SMCC HD90 and SMCC 90LM and the like.

The term "substantially in accordance" with reference to XRPD diffraction patterns means that allowance is made for variability in peak positions and relative intensities of the peaks. The ability to ascertain substantial identities of X-ray diffraction patterns is within the purview of one of ordinary skill in the art. For example, a typical precision of the 2-Theta values is in the range of ±0.2° 2-Theta. Thus, a diffraction peak that usually appears at 14.9° 2-Theta can appear between 14.7° and 15.1° 2-Theta on most X-ray diffractometers under standard conditions. Moreover, variability may also arise from the particular apparatus employed, as well as the degree of crystallinity in the sample, orientation, sample preparation and other factors. XRPD measurements are typically performed at RT, for example at a temperature of 20° C., and preferably also at a relative humidity of 40%.

As used herein, the term "substantially pure" with reference to a particular crystalline (polymorphic) form of ridinilazole is used to define one which includes less than 10%, preferably less than 5%, more preferably less than 3%, most preferably less than 1% by weight of any other physical form of ridinilazole.

As used herein the term "room temperature" (RT) relates to temperatures between 15 and 25° C.

The D$_{90}$ particle size is a parameter such that 90% by volume of particles are smaller in their longest dimension than that parameter, as measured by any conventional particle size measuring technique known to those skilled in the art. Such techniques include, for example, sedimentation field flow fractionation, photon correlation spectroscopy, light scattering (e.g. laser diffraction) and disk centrifugation.

The D$_{50}$ particle size of a composition is a parameter such that 50% by volume of particles in the composition are smaller in their longest dimension than that parameter, as measured by any conventional particle size measuring technique known to those skilled in the art (and as described above). D$_{50}$ particle size is therefore a measure of volume median particle size but is sometimes referred to as "average" or "mean" particle size.

The D$_{10}$ particle size of a composition is a parameter such that 10% by volume of particles in the composition are smaller in their longest dimension than that parameter, as measured by any conventional particle size measuring technique known to those skilled in the art (and as described above).

As used herein, the term "tableting composition" used in relation to compositions of the invention defines a composition comprising ridinilazole tetrahydrate which is suitable for compression into a tablet. Tableting compositions of the invention are typically suitable as a feed for a tablet press, for example a stamping or rotary tablet press. In preferred embodiments, tableting compositions of the invention are suitable for compression into a ridinilazole tetrahydrate tablet comprising an intragranular solid phase incorporated in an extragranular solid phase, wherein: (a) the intragranular phase comprises ridinilazole tetrahydrate crystal agglomerates having a particle size D$_{90}$ of 4-30 μm dispersed within a first pharmaceutically acceptable excipient system; and (b) the extragranular phase comprises a second pharmaceutically acceptable excipient system, wherein the first and second excipient systems are different.

"Therapeutically effective amount" refers to an amount of a compound or of a pharmaceutical composition useful for treating or ameliorating an identified disease or condition, or for exhibiting a detectable therapeutic or inhibitory effect. "Therapeutically effective amount" further includes within its meaning a non-toxic but sufficient amount of the particular drug to which it is referring to provide the desired therapeutic effect. The exact amount required will vary from subject to subject depending on factors such as the patient's general health, the patient's age, etc. The exact amounts will depend on the purpose of the treatment and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

Treat," "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

The abbreviation, "(w/w)" refers to the phrase "weight for weight", i.e., the proportion of a particular substance within a mixture, as measured by weight or mass or a weight amount of a component of the composition disclosed herein relative to the total weight amount of the composition. Accordingly, the quantity is unit less and represents a weight percentage amount of a component relative to the total weight of the composition. For example, a 2% (w/w) solution means 2 grams of solute is dissolved in 100 grams of solution.

It is to be understood, however, that the tableting compositions of the invention as defined herein may also be suitable for other uses. In particular, the tableting compositions of the invention may also be suitable for use as the basis of dosage forms other than tablets, including liquid suspensions, granule-filled capsules and granule-filled sachets (or other containers).

Methods of Manufacturing the Ridinilazole Tetrahydrate Tablets

Both, small scale (approx. 1 kg granulation, 6 litre granulator) and larger scale (approx. 3 kg and 9 kg granulation, 25 litre and 65 litre granulators respectively) syntheses are essentially the same and are described in the manufacturing process presented in FIG. 15.

Overall, process development studies indicated the importance of the wet massing step, including use of micronized API and the appropriate ratio of intragranular to extragranular phase of the final blend to be compressed into tablets of suitable hardness and disintegration time.

Prototype tablet process manufacturing trials demonstrated that the wet massing step is a critical one for the product, as the granulation end-point was reached in a short wetting rate window. Attempts employing reduced granulation water level (20% and 15%), to generate a less dense granulation confirmed that for the granulation step, the reduced water level could be effective and usually could produce well-formed granules. However, the reduction of the quantity of purified water added during the granulation step did not always lead to core tablets with good hardness and short disintegration times. Also, one lot of product evaluated using the process failed to produce suitable granules and tableting was not able to proceed.

It was considered that agglomerated particles in the API and the dominance of the API within the blend (approximately 65% by weight of the granulation blend) in the granulator during wet massing of the prototype tablet process may have been a contributor to the poor reproducibility of the granulation. Hence for the tablet process, studies were undertaken to try to improve the latitude in the granulation and reproducibility of granulation and dissolution.

Recognizing the presence of variable amounts of agglomerates in the API, it was determined to use micronized API. This would assure that the API particle characteristics were more consistent lot to lot, e.g. in terms of particle size distribution and may assist in reproducibility of the wet granulation step. To gain more latitude in the wet granulation step, a further portion of the excipients (other than magnesium stearate) were moved from the external phase to the wet granulation step internal phase, such that the internal phase now comprised 90% by weight of the final blend.

Small scale trials, (approximately 200 g granulation in a 1 L capacity granulator bowl), confirmed that latitude in granulation end point had been improved. Well-formed granules were produced over a range of 30% to 37% by weight added water during wet granulation and producing tablets of good hardness (approximately 170 N) with short disintegration times (approximately 5 minutes). The identified tableting manufacturing process was adapted to a 6 L (approximately 1 Kg granulation), 25 L (approximately 3 Kg granulation) and 65 L (approximately 9 Kg granulation) granulator bowl and this process was advanced to the manufacture larger scale supplies.

A conventional wet granulation approach to product manufacture was pursued to avoid flow problems that were observed in initial exploration of direct compression and roller compaction dry granulation alternatives. Initial work, described here as tablet development, focused on excipient choices and amounts, as well as initial wet granulation parameters (e.g. added water amount). Subsequent work to confirm process for the clinical trial formulation was subsequently undertaken to improve the performance of the granulation process.

The prototype wet granulation tablet formulation was identified after initial development and compatibility studies had been undertaken. Compatibility of ridinilazole tetrahydrate active substance with a range of excipients routinely utilized in tablet formulations was effectively demonstrated. The wet granulation formulation screening identified a lead formulation that produced granules which showed good flow and acceptable tablet processability at small scale at low compression force. The prototype tablet formulation demonstrated rapid disintegration and complete dispersion in less than 4 minutes. This was scaled up in order to progress a 1,000 tablets pilot run to enable samples to be placed onto a 6 months stability study. No significant changes to appearance, assay, related substances, hardness, moisture content or disintegration time were noted at either the long-term (25° C./60% RH) or accelerated (40° C./75% RH) condition, thus confirming stability of the prototype tablet formulation.

Additional development and optimization using small scale prototype tablet formulation was then pursued with the aim to identify a manufacturing process that would enable the production of robust tablets suitable for larger scale, high speed tablet presses. The prototype formulation was investigated in studies which evaluated variations to lactose:microcrystalline cellulose ratio, disintegrant amount, binder amount and water amount. Eleven formulations were manufactured and tested. Extremes and center point were also tested across the compression curves in order to understand the compaction behavior. Key outputs were run through a statistical software package in order to identify any trends with regards to critical quality attributes. Tablets from these studies were however found to have a longer disintegration time compared to the original process prototype tablets which required additional investigation.

Therefore, a second study, adopting a "one variable at a time" approach, was subsequently performed in order to establish a process for the prototype formulation which could produce a tablet which met the desired target product profile with respect to disintegration, dissolution, manufacturability and ability to produce a robust formulation for scale up. Binder quantity, water quantity, lactose distribution ratio (intragranular/extragranular) and disintegrant distribution ratio (intragranular/extragranular) were further evaluated in order to try to determine a final optimized process. However, these tablets showed challenges of granulation end point detection and consequent problems of flow on the tablet press at one extreme, and tablet crushing strength/disintegration at the other. Despite the challenges with the granulation process, it was possible to manufacture tablets which were placed on stability.

Consequently, to further assure tablet manufacturing process acceptability at a larger scale, and suitable for manufacture, further development of the granulation was undertaken. Without changing the quantitative and qualitative composition from that previously developed, by moving most of the excipients in the tablet to the intragranular phase and optimizing the particle size of the remaining excipients in the extragranular phase. Additionally by employing micronized controlled particle size ridinilazole tetrahydrate drug substance to provide for more reproducible drug substance characteristics during wet granulation, a process that had acceptable latitude for granulation end point based on water amount required and had good flow on the tablet press was produced.

Excipient Systems

The tablets and tableting compositions of the invention comprise two distinct pharmaceutically acceptable excipient systems, referenced herein as the first and second pharmaceutically acceptable excipient systems.

In the case of the ridinilazole tetrahydrate tablets of the invention, the first pharmaceutically acceptable excipient system forms part of an intragranular phase along with dispersed ridinilazole tetrahydrate crystal agglomerates, while the second pharmaceutically acceptable excipient system constitutes an extragranular phase in relation to the intragranular phase containing the API and first excipient system.

Analogously, in the case of the tableting compositions of the invention, the first pharmaceutically acceptable excipient system is present within granules together with dispersed ridinilazole tetrahydrate crystal agglomerates, and these granules are surrounded by the second pharmaceutically acceptable excipient system (which is therefore extragranular).

Each excipient system comprises at least one pharmaceutically acceptable excipient, though in preferred embodiments both excipient systems comprise two or more chemically and/or functionally distinct excipients.

The two excipient systems of the tablets and tableting compositions of the invention are distinct, or different. They may differ inter alia: (a) in relation to the identity of one or more of the excipient(s) present; (b) in relation to the number of chemically and/or functionally distinct excipients present; (c) in relation to the concentration of an excipient present; (d) in relation to the relative concentrations of two or more of the excipients present; and/or (e) in relation to the presence, or absence, of a distinct functional class of excipient.

In preferred embodiments, both first and second pharmaceutically acceptable excipient systems comprise a diluent. This diluent may be referenced herein as the "first diluent" when present in the first second pharmaceutically acceptable excipient system, and as the "second diluent" when present in the second pharmaceutically acceptable excipient system. Preferably, two distinct diluents are employed in one or both of the first and second excipient systems, and these may be referenced herein as first and second diluents, respectively.

In preferred embodiments, both first and second pharmaceutically acceptable excipient systems comprise a disintegrant. This disintegrant may be referenced herein as the "first disintegrant" when present in the first second pharmaceutically acceptable excipient system, and as the "second disintegrant" when present in the second pharmaceutically acceptable excipient system. Preferably, a single disintegrant is employed in one or both of the first and second excipient systems, and these may be referenced herein as first and second disintegrant, respectively. The first and second disintegrant may be the same or different, and in preferred embodiments the first and second disintegrant is the same.

In preferred embodiments, the first pharmaceutically acceptable excipient system contains a binder, while the second pharmaceutically acceptable excipient system does not contain a binder.

In preferred embodiments, the first pharmaceutically acceptable excipient system does not contain a lubricant, while the second pharmaceutically acceptable excipient system contains a lubricant.

Thus, in particularly preferred embodiments, the two excipient systems differ in relation to the presence/absence of two particular functional classes of excipient, these being binder and lubricant. Specifically, it is particularly preferred that: (a) the first pharmaceutically acceptable excipient system contains a binder and that this class of excipient is absent from the second excipient system, while (b) the second pharmaceutically acceptable excipient system contains a lubricant and that this class of excipient is absent from the first excipient system.

In various embodiments, depending on the first and second excipient systems use the tablet formulations can be delivered as immediate release, sustained released, extended release, delayed release, or a combination thereof.

Excipient Functional Classes

Diluents

As explained above, both first and second pharmaceutically acceptable excipient systems may comprise a diluent. Any suitable pharmaceutically acceptable diluent or combinations thereof may be used. These include diluents which comprise, consist of, or consist essentially of, lactose monohydrate and/or microcrystalline cellulose, for example lactose monohydrate and microcrystalline cellulose in combination.

In preferred embodiments, the first diluent comprises, consists of, or consists essentially of, a combination of lactose monohydrate 200M and Avicel PH101®. In other preferred embodiments, the second diluent comprises, consists of, or consists essentially of, a combination of lactose monohydrate 100M and Avicel PH102®.

Disintegrants

As explained above, both first and second pharmaceutically acceptable excipient systems may comprise a disintegrant. Any suitable pharmaceutically acceptable disintegrant, or combinations thereof, may be used. These include disintegrants selected from croscarmellose sodium, crospovidone, microcrystalline cellulose, polacrilin potassium, powdered cellulose, pregelatinized starch, sodium starch glycolate and starch.

Particularly preferred as first and second disintegrants is croscarmellose sodium, for example Ac Di Sol® or Primellose®. Croscarmellose sodium has been found to be unexpectedly advantageous as a disintegrant in the tablets and tableting compositions of the invention. Without wishing to be bound by any theory, it is believed that ionic interaction between ridinilazole tetrahydrate and croscarmellose sodium attendant on the formation of anionic hydrogels in contact with water (see e.g. Huang et al. (2006) Elimination of meformin-croscarmellose sodium interaction by competition Int J Pharm 311(1-2): 33-39). In particular, the inventors have unexpectedly noted improved disintegration times when using croscarmellose sodium as disintegrant when compared to otherwise identical tablets using crospovidone as disintegrant.

Binders

As explained above, the first pharmaceutically acceptable excipient system may contain a binder (while the second pharmaceutically acceptable excipient system preferably does not contain a binder). Any suitable pharmaceutically acceptable binder, or combinations thereof, may be used. Preferred binders comprise, consist of, or consist essentially of, a hydrophilic polymer.

Suitable binders may be selected from polyvinyl pyrrolidone (PVP), copovidone (PVP-polyvinyl acetate copolymer), partially gelatinized starch (PGS), and cellulose ethers. For example, the binder may comprise a cellulose ether selected from hydroxypropyl cellulose (HPC), methyl cellulose (MC), hydroxypropylmethyl cellulose (HPMC), ethylcellulose (EC) and sodium carboxymethyl cellulose (NaCMC).

In preferred embodiments, the binder comprises, consists of, or consists essentially of, hydroxypropylcellulose, this being present only in the first pharmaceutically acceptable excipient system (the second pharmaceutically acceptable excipient system being free of any binders).

Lubricants

As explained above, the second pharmaceutically acceptable excipient system may contain a lubricant (while the first pharmaceutically acceptable excipient system preferably does not contain a lubricant). Any suitable pharmaceutically acceptable lubricant, or combinations thereof, may be used.

Preferred lubricants may be selected from: (a) fatty acids; (b) metallic salts of fatty acids; (c) combinations of fatty acids and metallic salts thereof; (d) fatty acid esters; (e) metallic salts of fatty acid esters; and (f) inorganic materials and polymers.

Suitable fatty acid lubricants may be selected from: stearic acid, palmitic acid and myristic acid. Suitable metallic salts of fatty acids may be selected from magnesium stearate, calcium stearate and zinc stearate. Combinations of the foregoing are also suitable: for example, the lubricant may comprise a combination of stearic acid and magnesium stearate.

The lubricant comprises a fatty acid ester selected from glyceride esters and sugar esters. For example, the lubricant comprises a glyceride ester selected from glyceryl monostearate, glyceryl tribehenate, and glyceryl dibehenate. Also suitable is a sugar ester selected from sorbitan monostearate and sucrose monopalmitate. The lubricant may also comprise, consist of, or consist essentially of, sodium stearyl fumarate and/or lysine.

In preferred embodiments, the lubricant comprises, consists of, or consists essentially of, magnesium stearate. This is more preferably present only in the second pharmaceutically acceptable excipient system (the first pharmaceutically acceptable excipient system being free of any lubricants).

Active Pharmaceutical Ingredient (API)

The API present in the tablets and tableting compositions of the invention is ridinilazole tetrahydrate. As used herein, the term ridinilazole is used to define the compound 2,2'-di(pyridin-4-yl)-1H,1'H-5,5'-bibenzo[d]imidazole (which may also be known as 2,2'-di-4-pyridinyl-6,6'-bi-1H-benzimidazole; 5,5'-bis[2-(4-pyridinyl)-1H-benzimidazole]; 2,2'-bis(4-pyridyl)-3H,3'H-5,5'-bibenzimidazole; or 2-pyridin-4-yl-6-(2-pyridin-4-yl-3H-benzimidazol-5-yl)-1H-benzimidazole). The term also includes pharmaceutically acceptable derivatives, salts, hydrates, solvates, complexes, bioisosteres, metabolites or prodrugs of ridinilazole, as herein defined, for example, ridinilazole tetrahydrate.

The ridinilazole tetrahydrate present in the tablets and tableting compositions of the invention preferably takes the form of ridinilazole tetrahydrate crystal agglomorates. Particularly preferred is ridinilazole tetrahydrate Form A (as herein defined).

Thus, in the above ridinilazole tetrahydrate tablet formulations, the ridinilazole tetrahydrate API is preferably present in the form of ridinilazole tetrahydrate crystals Form A characterized by a powder X-ray diffractogram comprising characteristic peaks at 2-Theta angles of (11.02±0.2°), (16.53±0.2°) and (13.0±0.2°).

Particle Size

Ridinilazole tetrahydrate exhibits very low aqueous solubility and relatively poor wettability, and the present inventors have unexpectedly discovered that control of API particle size is important in controlling variability in the processability and performance of the tablet, tableting composition and processes of the invention, directly or indirectly impacting granule structure and thereby tablet quality.

In particular, it was found that ridinilazole tetrahydrate tablets manufactured using drug substance with crystal agglomerate particles having a $D_{90}$ outside of the about 10 to about 20 μm range (and in particular having a $D_{90}$ below 4 μm or above 30 μm) yielded tablets having properties which were unsuitable for drug product manufacture and performance (see Example 9, below).

In embodiments, the crystal agglomerates may have a particle size $D_{90}$ of about 5 μm to about 40 μm, and preferably have a particle size $D_{90}$ of about 10 to about 20 μm. In other embodiments, the crystal agglomerates may have a particle size $D_{90}$ of less than 40 μm, less than 35 μm, less than 30 μm, less than 25 μm, less than 20 μm, less than 15 μm, less than 10 μm, or less than 5 μm.

Thus, the ridinilazole tetrahydrate API is present in the tablets, tableting compositions and processes of the invention in the form of ridinilazole tetrahydrate agglomerates having a particle size $D_{90}$ of about 4 to about 30 μm, preferably a $D_{90}$ of 7-25 μm, more preferably a $D_{90}$ of 10-20 μm).

Size reduction of the ridinilazole tetrahydrate API (for example, when provided in the form of crystalline ridinilazole tetrahydrate Form A) can be achieved by any convenient method, including milling, grinding, sieving and/or screening. Preferred is size reduction by air jet milling.

API particle size can be determined using any convenient and well-documented analytical technique. These techniques include sedimentation field flow fractionation, photon correlation spectroscopy, light scattering (e.g. laser diffraction) and disk centrifugation. Preferred is dry laser diffraction as described herein.

Secondary Agglomeration, Pre-Blending and API Distribution

Stationary bulk solids such as dry powder or granules (i.e. aggregates) tend to form agglomerates driven by more or less strong attractive forces. The strength of these forces depend on material properties, surface conditions, residual moisture and particle size, and may involve Van der Waals forces, capillary forces, and/or electrostatic and magnetic forces of attraction. In general, the smaller the particles, the greater the tendency to bind.

The inventors have unexpectedly discovered that size-reduced API having the desired particle size $D_{90}$ of 4-30 μm have a marked tendency to re-agglomorate to form secondary, "soft agglomerates". Specifically, ridinilazole tetrahydrate API that has undergone a particle size reduction operation (such as air jet milling or other micronization methods) is a very cohesive, poorly flowing powder that exhibits a static charge and a tendency to re-associate to form secondary "soft agglomerates".

These secondary soft agglomerates are problematic, in that they prevent efficient blending with the first excipient systems of the invention. It has therefore been found that it is important to break up the soft agglomerates before combining the ridinilazole tetrahydrate into the first excipient blend for granulation, to ensure they do not persist to any degree following the wet granulation and drying processes. This avoids the presence of "hot spots" of poorly distributed ridinilazole tetrahydrate in the finished granules and tablets, which leads to undesirable variability in the uniformity of API in tablets and tableting compositions.

It has been found that sieve or screening size-reduced ridinilazole tetrahydrate having a particle size $D_{90}$ of 4-30 μm is a very difficult and time consuming operation, whether done by hand or mechanically (e.g. using a cone mill or oscillator), as the soft agglomerates of ridinilazole tetrahydrate particles cause blockage and blinding of sieve and screen apertures, smearing out across the surfaces thereof. This ultimately leads to blockages that require process interruptions to permit cleaning/clearing, and also causes incomplete and slow transfer of powder through the sieve. Sieving and screening is therefore difficult, slow or even impossible.

This problem can be overcome by making a preliminary blend of the ridinilazole tetrahydrate crystal agglomerate particles having a particle size $D_{90}$ of 4-30 μm with a fraction of a first pharmaceutically acceptable intragranular excipient system (e.g. a subset of the constituent excipients of a first excipient system as herein defined). For example, it has been found that blending the ridinilazole tetrahydrate particles with all of the first excipients except for some or all of the first diluent (for example, the microcrystalline cellulose of the preferred embodiments) to form an initial, intermediate, blend allows effective and easy sieving of that intermediate blend, permitting effective break-up of any soft agglomerates of ridinilazole tetrahydrate.

The sieve can then be "washed" or "flushed through" with the reserved diluent (e.g. the microcrystalline cellulose of the preferred embodiments), which has been found to be effective to transfer of any granule blend of first excipients and API remaining on the sieve surface into the final blend (e.g. microcrystalline cellulose, or other first diluent, passing through the sieve can be combined with the rest of the ridinilazole tetrahydrate mixture already sieved and the whole material then finally mixed to yield a final blend for granulation).

Such processes ensure good, uniform distribution of ridinilazole tetrahydrate API within the intragranular phase of the tablet of the invention and within granules of the various compositions of the invention.

The discovery described above finds application in processes for producing the compositions of the invention. For example, it finds application in a process for producing a granular ridinilazole tetrahydrate composition according to the third aspect of the invention described above. In such cases, the ridinilazole tetrahydrate agglomerates are first mixed with an initial fraction of a first pharmaceutically acceptable intragranular excipient system to form an initial pre-granulation mix, which pre-granulation mix is then screened or sieved to form a screened initial pre-granulation mix, before a second fraction of the first pharmaceutically acceptable intragranular excipient system, is passed through the same screen or sieve to form a screened second fraction. The screened initial pre-granulation mix can then be mixed with the screened second excipient fraction to form a final pre-granulation mix for granulation according to step (c) of the third aspect of the invention. In this way, "hot spots" arising from soft agglomerates of ridinilazole tetrahydrate may be avoided, and a more uniform distribution of ridinilazole tetrahydrate API in the tableting composition (and ultimately, the ridinilazole tetrahydrate tablet) is achieved.

Pre-Blending and API Distribution in Other Particulate or Granular Ridinilazole Tetrahydrate Compositions As explained above, the tableting compositions of the invention may also be suitable for use as the basis of dosage forms other than tablets, including liquid suspensions, granule-filled capsules and granule-filled sachets (or other containers). Thus, the recognition of the potential problems arising from re-agglomeration in size-reduced ridinilazole tetrahydrate particulate compositions, and the discovery of the advantages associated with measures effective to prevent, remove or break up secondary soft-agglomerates (e.g. via the pre-blending steps described above), also find application in the production of ridinilazole tetrahydrate compositions sharing the composition of the tableting compositions of the invention but which are suitable for uses other than tableting (including other oral dosage forms such as liquid suspensions, granule-filled capsules and granule-filled sachets).

The discovery described above therefore find broad application in the production of granular or particulate ridinilazole tetrahydrate compositions in which secondary soft agglomerates (formed by re-agglomeration of size-reduced API as described above) are substantially absent. The invention therefore also contemplates granular or particulate ridinilazole tetrahydrate compositions comprising crystal agglomerates of crystalline ridinilazole tetrahydrate having a particle size $D_{90}$ of 4-30 μm in which soft secondary agglomerate arising from re-agglomeration of said crystal agglomerates are substantially absent.

Such granular or particulate ridinilazole tetrahydrate compositions are preferably, but not necessarily, suitable for compression into a tablet. They may, for example, be suitable for uses other than tableting. Such uses include oral and non-oral ridinilazole tetrahydrate pharmaceutical compositions. For example, the granular or particulate ridinilazole tetrahydrate compositions of the invention may take the form of, or find application in the preparation of, pharmaceutical formulations other than tablets, including liquid suspensions, granule-filled capsules and granule-filled sachets (or other containers).

Tablet Formulations

Ridinilazole tetrahydrate tablets of the invention comprise an intragranular solid phase incorporated in an extragranular solid phase, wherein: (a) the intragranular phase comprises ridinilazole tetrahydrate agglomerates having a particle size $D_{90}$ of about 4 to about 30 μm dispersed within a first pharmaceutically acceptable excipient system; and (b) the extragranular phase comprises a second pharmaceutically acceptable excipient system, wherein the first and second excipient systems are different. Preferred ridinilazole tetrahydrate tablets of the invention have the following composition:

| Component | Function |
|---|---|
| Intragranular Phase | |
| Ridinilazole (tetrahydrate) | API |
| Lactose monohydrate | First diluent |

-continued

| Component | Function |
|---|---|
| Microcrystalline Cellulose | First diluent |
| Hydroxypropylcellulose | Binder |
| Croscarmellose sodium | First disintegrant |
| Extragranular Phase | |
| Lactose monohydrate | Second diluent |
| Microcrystalline Cellulose | Second diluent |
| Croscarmellose sodium | Second disintegrant |
| Magnesium stearate | Lubricant |

More preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) | API | 50 ± 20 |
| Lactose monohydrate | First diluent | 25 ± 10 |
| Microcrystalline Cellulose | First diluent | 10 ± 5 |
| Hydroxypropylcellulose | Binder | 3 ± 1.5 |
| Croscarmellose sodium | First disintegrant | 2 ± 1 |
| Extragranular Phase | | |
| Lactose monohydrate | Second diluent | 4 ± 2 |
| Microcrystalline Cellulose | Second diluent | 1.5 ± 1 |
| Croscarmellose sodium | Second disintegrant | 3 ± 2 |
| Magnesium stearate | Lubricant | 1 ± 0.5 |

[1]It is to be understood that selections may be selected within the ranges specified provided that the % Formula w/w totals 100.

Yet more preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) | API | 50 ± 10 |
| Lactose monohydrate | First diluent | 25 ± 5 |
| Microcrystalline Cellulose | First diluent | 10 ± 2.5 |
| Hydroxypropylcellulose | Binder | 3 ± 0.75 |
| Croscarmellose sodium | First disintegrant | 2 ± 0.5 |
| Extragranular Phase | | |
| Lactose monohydrate | Second diluent | 4 ± 1 |
| Microcrystalline Cellulose | Second diluent | 1.5 ± 0.5 |
| Croscarmellose sodium | Second disintegrant | 3 ± 1 |
| Magnesium stearate | Lubricant | 1 ± 0.2 |

[1]It is to be understood that selections may be selected within the ranges specified provided that the % Formula w/w values total 100.

Yet more preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) | API | 50 |
| Lactose monohydrate | First diluent | 25 |
| Microcrystalline Cellulose | First diluent | 10 |
| Hydroxypropylcellulose | Binder | 3 |
| Croscarmellose sodium | First disintegrant | 2 |
| Extragranular Phase | | |
| Lactose monohydrate | Second diluent | 4 |
| Microcrystalline Cellulose | Second diluent | 1.5 |
| Croscarmellose sodium | Second disintegrant | 3 |
| Magnesium stearate | Lubricant | 1 |

[1]It is to be understood that the given % values may each be independently varied by ±10%, ±5%, ±2% or ±1%, provided that the % Formula w/w values total 100.

Yet more preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) | API | 50.00 |
| Lactose monohydrate | First diluent | 25.49 |
| Microcrystalline Cellulose | First diluent | 9.51 |
| Hydroxypropylcellulose | Binder | 3.00 |
| Croscarmellose sodium | First disintegrant | 2.00 |
| Extragranular Phase | | |
| Lactose monohydrate | Second diluent | 4.37 |
| Microcrystalline Cellulose | Second diluent | 1.63 |
| Croscarmellose sodium | Second disintegrant | 3.00 |
| Magnesium stearate | Lubricant | 1.00 |

[1]It is to be understood that the given % values may each be independently varied by ±5%, ±2% or ±1%, provided that the % Formula w/w values total 100.

Yet more preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) | API | 50.00 |
| Lactose monohydrate | First diluent | 25.49 |
| Microcrystalline Cellulose | First diluent | 9.51 |
| Hydroxypropylcellulose | Binder | 3.00 |
| Croscarmellose sodium | First disintegrant | 2.00 |
| Extragranular Phase | | |
| Lactose monohydrate | Second diluent | 4.37 |
| Microcrystalline Cellulose | Second diluent | 1.63 |
| Croscarmellose sodium | Second disintegrant | 3.00 |
| Magnesium stearate | Lubricant | 1.00 |

[1]It is to be understood that the given % values may each be independently varied by ±2% or ±1%, provided that the % Formula w/w values total 100.

Yet more preferred ridinilazole tetrahydrate tablets of the invention have the following composition:

| Component | Function | % Formula (% w/w)[1] |
|---|---|---|
| Intragranular Phase | | |
| Ridinilazole (tetrahydrate) crystal agglomerates Form A | API | 50.00 |
| Lactose monohydrate | First diluent | 25.49 |
| Microcrystalline Cellulose | First diluent | 9.51 |
| Hydroxypropylcellulose | Binder | 3.00 |
| Croscarmellose sodium | First disintegrant | 2.00 |
| Extragranular Phase | | |
| Lactose monohydrate | Second diluent | 4.37 |
| Microcrystalline Cellulose | Second diluent | 1.63 |

| Component | Function | % Formula (% w/w)[1] |
|---|---|---|
| Croscarmellose sodium | Second disintegrant | 3.00 |
| Magnesium stearate | Lubricant | 1.00 |

[1] It is to be understood that the given % values may each be independently varied by ±2% or ±1%, provided that the % Formula w/w values total 100.

In the above exemplified tablet formulations, the tablet preferably further comprises a coating, for example a water-soluble polymer film.

In the above exemplified tablet formulations, the tablet preferably contains about 100 to about 400 mg of ridinilazole tetrahydrate, more preferably about 100 to about 300 mg of ridinilazole tetrahydrate, yet more preferably about 150 to about 250 mg of ridinilazole tetrahydrate, most preferably about 200 mg of ridinilazole tetrahydrate. One of ordinary skill in the art will be able to calculate that, for example, 200 mg of ridinilazole tetrahydrate is equivalent to 169 mg of ridinilazole on an anhydrous basis.

A particularly preferred tablet formulation has the following composition:

| Component | Component Function | Quantity (mg) |
|---|---|---|
| *Intragranular Phase* | | |
| Ridinilazole tetrahydrate[2] | API | 200.00 |
| Lactose monohydrate | First diluent | 101.96 |
| Microcrystalline Cellulose | First diluent | 38.04 |
| Hydroxypropylcellulose | Binder | 12.00 |
| Croscarmellose sodium | First disintegrant | 8.00 |
| *Extragranular Phase* | | |
| Lactose monohydrate | Second diluent | 17.48 |
| Microcrystalline Cellulose | Second diluent | 6.52 |
| Croscarmellose sodium | Second disintegrant | 12.00 |
| Magnesium stearate | Lubricant | 4.00 |
| TOTAL | | 400.00 |

[1] It is to be understood that the given % values may each be independently varied by ±2% or ±1%, provided that the % Formula w/w values total 100.

2. The quantity 200 mg of ridinilazole tetrahydrate is equivalent to 169 mg of ridinilazole on an anhydrous basis.

In the above ridinilazole tetrahydrate tablet formulations, the ridinilazole tetrahydrate API is preferably present in the form of ridinilazole tetrahydrate crystals Form A characterized by a powder X-ray diffractogram comprising characteristic peaks at 2-Theta angles of (11.02±0.2°), (16.53±0.2°) and (13.0±0.2°).

Most preferred tablet formulations have one of the following compositions:

| Component | Component Function | Quantity (mg) |
|---|---|---|
| *Intragranular Phase* | | |
| Ridinilazole tetrahydrate crystal agglomerates Form A[2] | API | 200.00 |
| Lactose monohydrate 200M | First diluent | 101.96 |
| Microcrystalline Cellulose (Avicel PH101) | First diluent | 38.04 |
| Hydroxypropylcellulose | Binder | 12.00 |
| Croscarmellose sodium | First disintegrant | 8.00 |
| *Extragranular Phase* | | |
| Lactose monohydrate 100M | Second diluent | 17.48 |
| Microcrystalline Cellulose (Avicel PH102) | Second diluent | 6.52 |
| Croscarmellose sodium | Second disintegrant | 12.00 |
| Magnesium stearate | Lubricant | 4.00 |
| TOTAL | | 400.00 |
| *Coating* | | |
| Opadry II Brown | Film Coat | 12.00 |
| TOTAL | | 412.00 |

[1] It is to be understood that the given % values may each be independently varied by ±2% or ±1%, provided that the % Formula w/w values total 100.

2. The quantity 200 mg of ridinilazole tetrahydrate Form A is equivalent to 169 mg of ridinilazole on an anhydrous basis.

| Component | Component Function | Quantity (mg) |
|---|---|---|
| *Intragranular Phase* | | |
| Ridinilazole tetrahydrate crystal agglomerates Form A[2] | API | 200.00 |
| Lactose monohydrate 200M | First diluent | 101.96 |
| Microcrystalline Cellulose (Avicel PH101) | First diluent | 38.04 |
| Hydroxypropylcellulose | Binder | 12.00 |
| Croscarmellose sodium | First disintegrant | 8.00 |
| Purified Water | | — |
| *Extragranular Phase* | | |
| Lactose monohydrate 100M | Second diluent | 17.48 |
| Microcrystalline Cellulose | Second diluent | 6.52 |
| Croscarmellose sodium | Second disintegrant | 12.00 |
| Magnesium stearate | Lubricant | 4.00 |
| TOTAL | | 400.00 |
| *Coating* | | |
| Opadry II Yellow 33G220012 | Film Coat | 12.00 |
| Purified Water | | — |
| TOTAL | | 412.00 |

Methods of Treatment

The formulations described comprising ridinilazole tetrahydrate (e.g., ridinilazole tetrahydrate Form A) may be utilized for the treatment or elimination of *Clostridium difficile* infection (CDI) and/or one or more *Clostridioides difficile*-associated diseases (CDAD). In embodiments, the CDI comprises toxin A and/or toxin B *C. difficile* in the stool. In embodiments, a subject in need thereof is administered a composition comprising ridinilazole tetrahydrate. In embodiments the composition comprises a ridinilazole tetrahydrate tablet as described herein. The administering may be effective to reduce or eliminate CDI and/or CDAD in a subject in need thereof.

In embodiments, a subject in need thereof is treated with a therapeutically effective amount of ridinilazole tetrahydrate (e.g., ridinilazole tetrahydrate Form A). In embodiments, a subject in need thereof is treated with a therapeutically effective amount of ridinilazole, wherein the therapeutically effective amount is sufficient to reduce or eliminate at least one symptom of CDI and/or CDAD. In embodiments, a therapeutically effective amount comprises at least about, at most about, or about 200 mg of ridinilazole tetrahydrate one or more times per day. In embodiments, a therapeutically effective amount comprises about 10, 25, 50, 75, 100, 120, 140, 160, 180, 185, 190, 191, 192, 193, 194, 195, 196, 197, 198, 199, 200, 201, 202, 203, 204, 205, 206, 207, 208, 209, 210, 220, 230, 240, 250, 275, 300, 350, 400, 450, or 500 mg of ridinilazole tetrahydrate (e.g., ridinilazole tetrahydrate Form A).

One of ordinary skill in the art will understand, for example, that 100 mg of ridinilazole tetrahydrate is equivalent to 84.5 mg of ridinilazole on an anhydrous basis (and, e.g., 200 mg ridinilazole tetrahydrate is equivalent to 169 mg anhydrous ridinilazole).

Accordingly, in certain embodiments, the administration of an amount of ridinilazole tetrahydrate Form A is equivalent to administering a subject about 8.45, 17, 25.5, 43, 76, 84.5, 93, 101, 110, 118, 126.5, 135, 143.5, 152, 160.5, 169, 178.5, 190, 200, 210, 220, 230, 240, 250, 275, 300, 350, 400, 450 mg of ridinilazole content on an anhydrous basis.

In embodiments, a subject in need thereof is administered ridinilazole tetrahydrate for any number of days. In embodiments, ridinilazole tetrahydrate is administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, or up to 30 days. In embodiments, ridinilazole tetrahydrate is administered for about 10 days. In embodiments, ridinilazole tetrahydrate is administered for about 5-10 days. In embodiments, ridinilazole tetrahydrate is administered for about 5-20 days. In embodiments, ridinilazole tetrahydrate is administered multiple times a day. For example, ridinilazole tetrahydrate can be administered once, twice, three times, four times, five times, or six times daily, preferably twice a day. In embodiments, ridinilazole tetrahydrate is administered every 12 hours. In embodiments, ridinilazole tetrahydrate is administered until CDI and/or CDAD is resolved. In embodiments, ridinilazole tetrahydrate is administered until a symptom of ridinilazole tetrahydrate is reduced or eliminated.

In embodiments, the administration of ridinilazole tetrahydrate is effective in reducing CDI and/or CDAD as determined by reduced or eliminated symptoms associated with CDI including but not limited to diarrhea (e.g., unformed bowel movement), fever, stomach tenderness, loss of appetite, nausea, and combinations thereof. In embodiments, administration of ridinilazole tetrahydrate is effective in reducing a symptom of CDI and/or CDAD by at least about 1 day as compared to an otherwise comparable subject lacking the administering. In embodiments, administration of ridinilazole tetrahydrate is effective in reducing a symptom of CDI and/or CDAD by at least about 1 day, 2 days, 3 days, 4 days, or 5 consecutive days as compared to an otherwise comparable subject lacking the administering.

In embodiments, the administration of ridinilazole tetrahydrate is effective in reducing CDI and/or CDAD as determined by reduced frequency of unformed bowel movements (UBMs) by the subject as compared to before the administration. In embodiments, administration of ridinilazole tetrahydrate is effective in eliminating CDI and/or CDAD in a subject in need thereof as determined by resolution of unformed bowel movement (UBM). In embodiments, administration of ridinilazole tetrahydrate is effective in reducing detection of a UBM by at least about 1 day as compared to an otherwise comparable subject lacking the administering. In embodiments, administration of ridinilazole tetrahydrate is effective in reducing detection of a UBM by at least about 1 day, 2 days, 3 days, 4 days, or 5 consecutive days as compared to an otherwise comparable subject lacking the administering. In embodiments, administration of ridinilazole tetrahydrate is effective in reducing recurrence of an episode of diarrhoea (e.g., over about 3 UBMs) in a 1-day period. In embodiments, a subject in need thereof achieves a clinical response following administration of ridinilazole tetrahydrate. In embodiments, a subject in need thereof achieves no recurrence of CDI and/or CDAD through about 10 days, 20 days, 30 days, 40 days, 50 days, 60 days, 70 days, 80 days, 90 days, 100 days, 110 days, 120 days, 130 days, 140 days, 150 days, 160 days, 170 days, 180 days, 190 days, or 200 days post treatment. In embodiments a subject in need thereof achieves no recurrence of CDI and/or CDAD for at least about 30 days or 90 days post treatment.

In embodiments, the administration of ridinilazole tetrahydrate is effective in reducing CDI and/or CDAD as determined by reduced frequency of unformed bowel movements (UBMs) by the subject as compared to an otherwise comparable subject administered vancomycin. In embodiments, administration of ridinilazole tetrahydrate is effective in reducing detection of a UBM by at least about 1 day as compared to an otherwise comparable subject administered vancomycin. In embodiments, administration of ridinilazole tetrahydrate is effective in reducing detection of a UBM by at least about 1 day, 2 days, 3 days, 4 days, or 5 consecutive days as compared to an otherwise comparable subject administered vancomycin. In embodiments, administration of ridinilazole tetrahydrate is effective in reducing recurrence of an episode of diarrhoea (e.g., over about 3 UBMs) in a 1-day period as compared to an otherwise comparable subject administered vancomycin.

Figure 16:
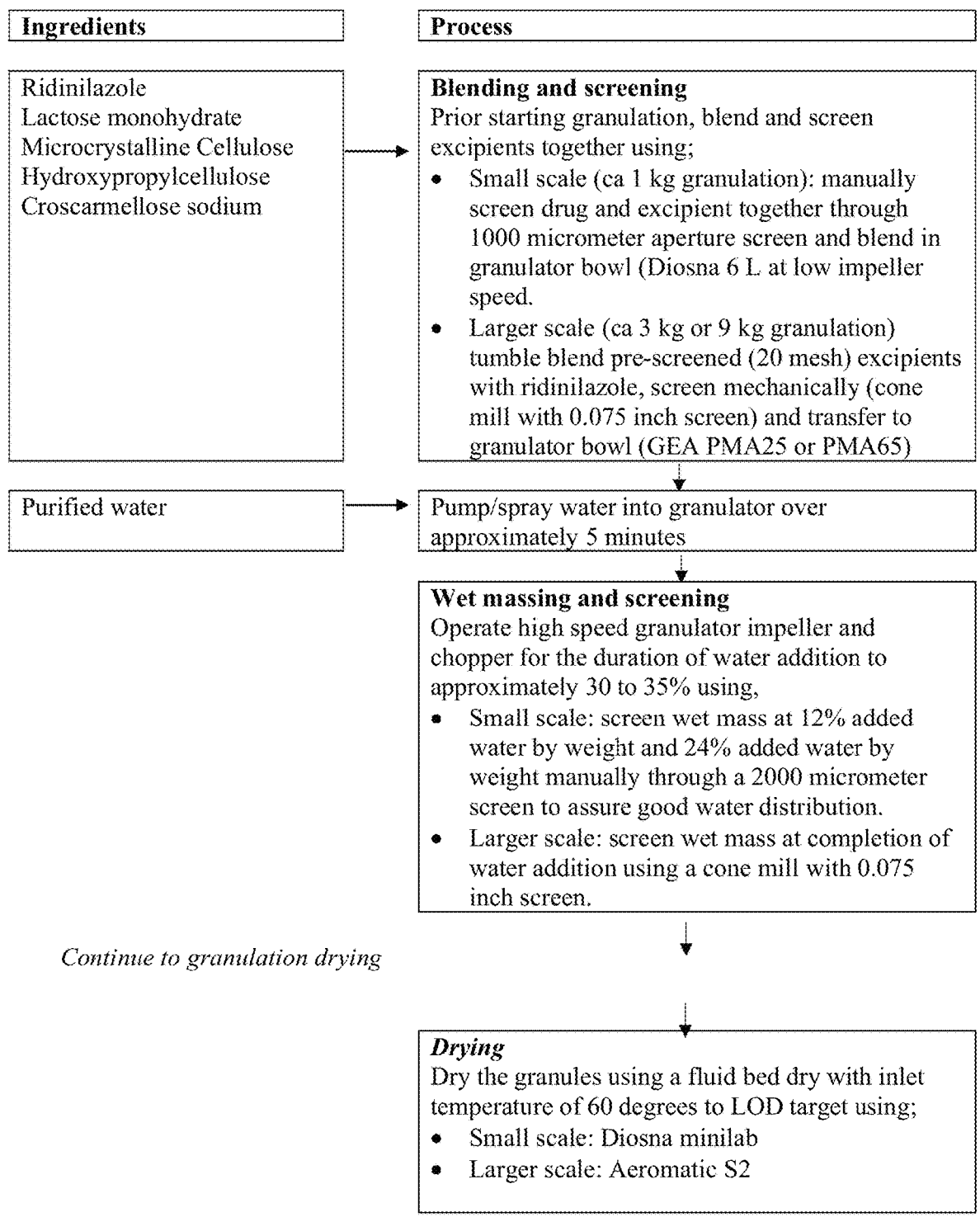
FIG. 16 shows an exemplary manufacturing process for ridinilazole tetrahydrate 200 mg tablets.
Figure 16:
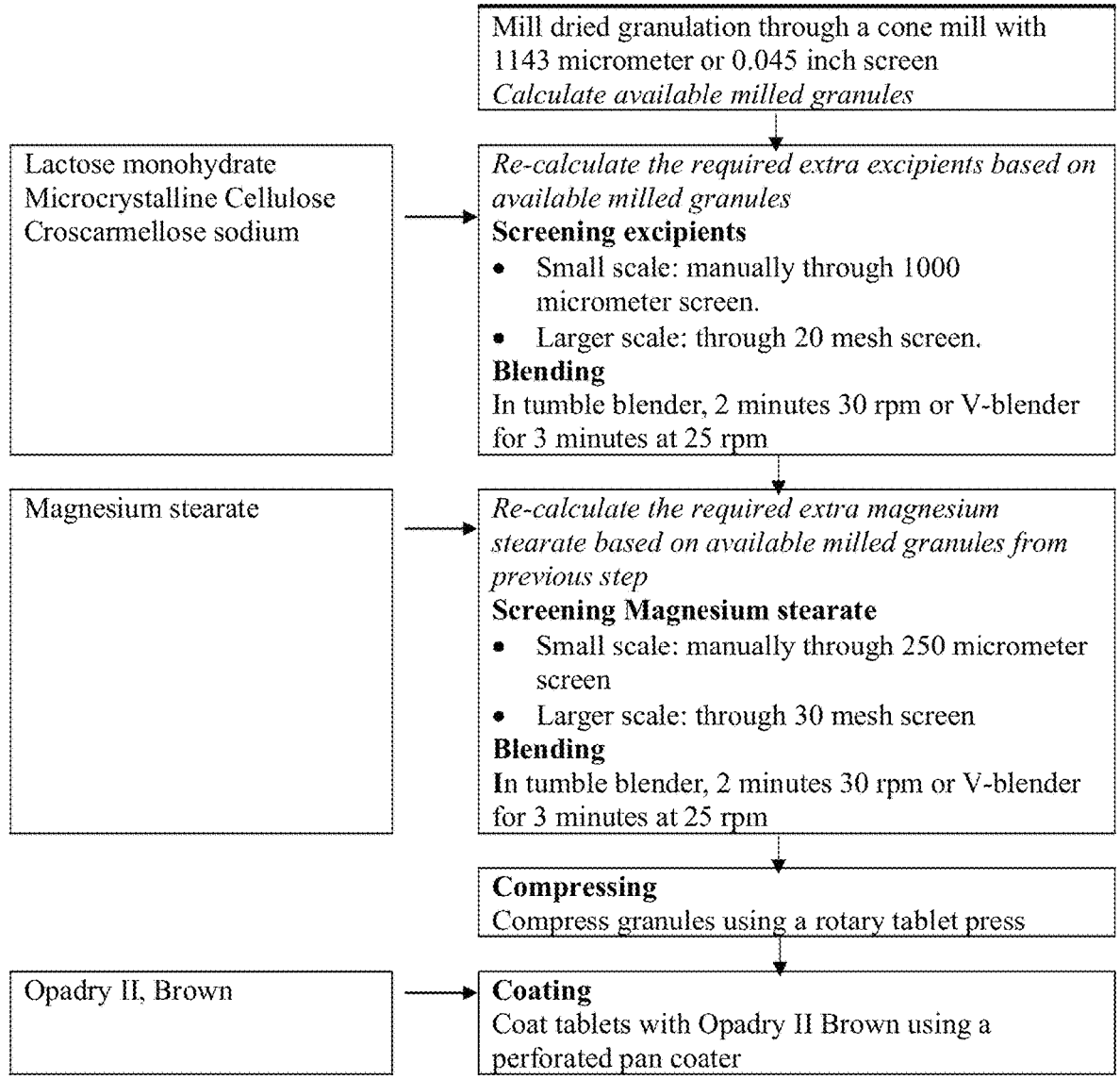

UBMs can be determined by way of the Bristol Stool Chart, see FIG. 16. In embodiments, a UBM comprises a type 5, 6, or 7 bowel movement in the Bristol Stool Chart. In embodiments, administration of ridinilazole tetrahydrate is effective in reducing frequency (in time) or detection of a UBM in a subject in need thereof. In embodiments, administration of ridinilazole tetrahydrate is effective in reverting a subject in need thereof bowel movements from a type 5, 6, or 7 to a type selected from the group consisting of 1, 2, 3, and 4. In embodiments, administration of ridinilazole tetrahydrate is effective in reverting a bowel movement type by at least about 1, 2, 3, 4, 5, or 6 types on the Bristol Stool Chart as compared to an otherwise comparable subject lacking the administration.

In embodiments, a subject in need thereof has previously been administered an antibiotic. In embodiments, the antibiotic is selected from the group consisting of: ampicillin, amoxicillin, cephalosporins, and clindamycin. However, any antibiotic is contemplated. In embodiments, a subject is co-treated with ridinilazole tetrahydrate and at least one additional therapeutic. In embodiments, the one additional therapeutic comprises an antibiotic. In embodiments, a subject in need thereof has previously been administered an antibiotic that is not ridinilazole tetrahydrate. In embodiments, a subject in need thereof has previously been administered vancomycin.

In embodiments, a subject in need thereof has been hospitalized or is hospitalized. In embodiments, a subject in need thereof has antibiotic-resistant *C. difficile*. In embodiments, a subject in need thereof is immunosuppressed. In embodiments, a subject in need thereof is undergoing a cancer chemotherapy.

In embodiments, CDI is detected using an in vitro assay. Suitable in vitro assays that can be utilized include but are not limited to: ELISA, latex agglutination assay, cell cytotoxicity assay, PCR, *C. difficile* culture, and combinations thereof.

EXAMPLES

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Methods

Water Activity ($A_w$)

Water activity coefficient and water activity were calculated using UNIFAC Activity Coefficient Calculator (Choy, B.; Reible, D. (1996). UNIFAC Activity Coefficient Calculator (Version 3.0, 1996) [Software]. University of Sydney, Australia and Louisiana State University, USA).

X-Ray Powder Diffraction (XRPD)

XRPD analyses were performed using a Panalytical Xpert Pro diffractometer equipped with a Cu X-ray tube and a Pixcel detector system. The isothermal samples were analysed in transmission mode and held between low density polyethylene films. The XRPD program used range 3-40° 2θ, step size 0.013°, counting time 99 sec, ~22 min run time. XRPD patterns were sorted using HighScore Plus 2.2c software.

Carbon (Norit®) treatment: Crude ridinilazole is dissolved in methanol plus 30% sodium methoxide, the resulting solution treated with Norit® SX Plus (0-0.5 wt) and the mixture stirred. The Norit® is then removed by filtration through a filter aid. To the filtrate is then added water followed by acetic acid in order to precipitate purified ridinilazole.

In Vitro Dissolution Analysis

Measured by HPLC using 2.5% sodium lauryl sulfate (SLS) in 0.01N HCl with the dissolution parameters as shown in the table below:

Degassed dissolution medium (1 litre) is placed into dissolution vessels and equilibrated to 37±0.5° C. Tablets for analysis are dropped into the dissolution vessel and allowed to sink to the bottom of the vessel. Paddle rotation (100 rpm) is then started. Using a syringe fitted with a stainless-steel cannula and full flow filter, 5 mL of the solution is withdrawn from a zone midway between the surface of the dissolution medium and the top of the paddle, not less than 1 cm from the vessel wall at 15, 30, 45 and 60 minutes. After 60 minutes, the rotation speed is increased to 250 rpm and rotate for 15 minutes, and then 5 mL of solution is withdrawn from the vessel. The solution is then filtered through an Acrodisc 25 mm syringe filter with 1 μm Glass fiber membrane, discarding the first 3 mL of the filtrate, and the remaining filtrate collected into an HPLC vial for analysis.

Ridinilazole Crystal Agglomerate Particle Sizing

This was carried out by laser diffraction using a Malvern 2000 dry disperser. The settings used for sizing are set out below:

| Instrument: | Malvern Mastersizer dry dispersion |
|---|---|
| Balance: | Minimum 2-place |
| Instrument Method | |
| Accessory Name: | Scirocco 2000 |
| Mode: | General purpose |
| Calculation sensitivity: only) | Normal (select 'Fine Power' for micronized samples |
| Sample Refractive Index: | 1.704 |
| Particle Absorption: | 0.01 |
| Obscuration Limits: | 0.1% to 6.0% (if achievable) |
| Vibration Feed Rate: | 45% |
| Mesh Size: | Large mesh, 1.6 mm |
| Sample Measurement Time: | 20 seconds |
| Dispersive Air Pressure: | 2 bar |
| Sample Tray: | General purpose (<200 g) |
| Aliquots: | 3 per method |
| Measurements: | 1 per aliquot |
| Background Time: | 3 seconds |
| Measurement Snaps: | 20,000 |
| Background Snaps: | 3,000 |

Sample preparation—Triplicate

Invert sample jar or vial 10 times. Weigh approximately 2 g of sample and transfer to the sample tray. Evenly disperse sample in sample tray.

Example 1: Production of Ridinilazole Form a Tetrahydrate Crystal Agglomerates

Reaction: The Reaction Flask was Charged with 4-cyanopyridine (0.85 kg), and MeOH (5.4 kg) and NAM-30 (NaOMe as 30 wt % solution in MeOH; 0.5 eq; 0.15 kg) was dosed in. The resulting mixture was heated at 60° C. for 10 min. and then cooled. This solution was added to a mixture of 3,3'-diaminobenzidine (DAB) (0.35 kg) and acetic acid (0.25 kg) in MeOH (1l) at 60° C. in 1 h. The mixture was then heated for 2 h. The reaction mixture was allowed to cool to ambient temperature overnight. The crystalline mass was filtered and washed with MeOH (1.4 L) and sucked dry on the filter.

Purification: The Norit treatment was conducted 4 times.

Polymorph formation: The reslurry in 20 vols of 1:3 WFI water: MeOH afforded the desired polymorph, drying was conducted in a vacuum drying oven @ ambient temperature and a nitrogen purge for 6 days.

XRPD analysis showed that this process yielded crystal agglomerates of hydrated ridinilazole Form A (see FIG. 1). The reflections are shown in the Table 1 below:

TABLE 1

Ridinilazole Tetrahydrate Form A 2-Theta °
Angle 2-Theta °
(Form A)

| |
|---|
| 4.94 |
| 5.09 |
| 5.51 |
| 6.13 |
| 6.53 |
| 8.13 |
| 8.62 |
| 9.82 |
| 10.5 |
| 11.02 |
| 11.34 |
| 12.26 |
| 13 |
| 13.54 |
| 14.23 |
| 15.07 |
| 15.62 |
| 16.53 |
| 17.28 |
| 17.84 |
| 18.5 |
| 18.6 |
| 19.28 |
| 19.64 |
| 20.31 |
| 21.6 |
| 22.14 |
| 22.33 |
| 22.77 |
| 22.89 |
| 23.05 |

TABLE 1-continued

Ridinilazole Tetrahydrate Form
A 2-Theta °
Angle 2-Theta °
(Form A)

23.73
24.11
24.71
25.23
25.5
25.77
26.75
26.98
27.38
27.85
28.51
29.26
29.76
29.87
30.6
31.1
31.43
31.88
32.87
34
34.19
35.24
35.42
35.94
36.99
37.74
38.22
39.16
39.68
39.83

The crystal agglomerates were then air jet milled to the target particle size ($D_{90}$ of about 4 to about 30 μm, preferably a $D_{90}$ of about 7 to about 25 μm, more preferably a $D_{90}$ of about 10 to about 20 μm).

Example 2: Crystal Structure of Ridinilazole Tetrahydrate Form A

Single crystals of ridinilazole Form A were grown via liquid diffusion at RT of a solution of ridinilazole in NMP/dioxane using chloroform as antisolvent. A needle crystal specimen, approximate dimensions 0.380 mm×0.015 mm×0.010 mm, was used for the X-ray crystallographic analysis on beamline 119 at Diamond Light Source.

Figure 2:
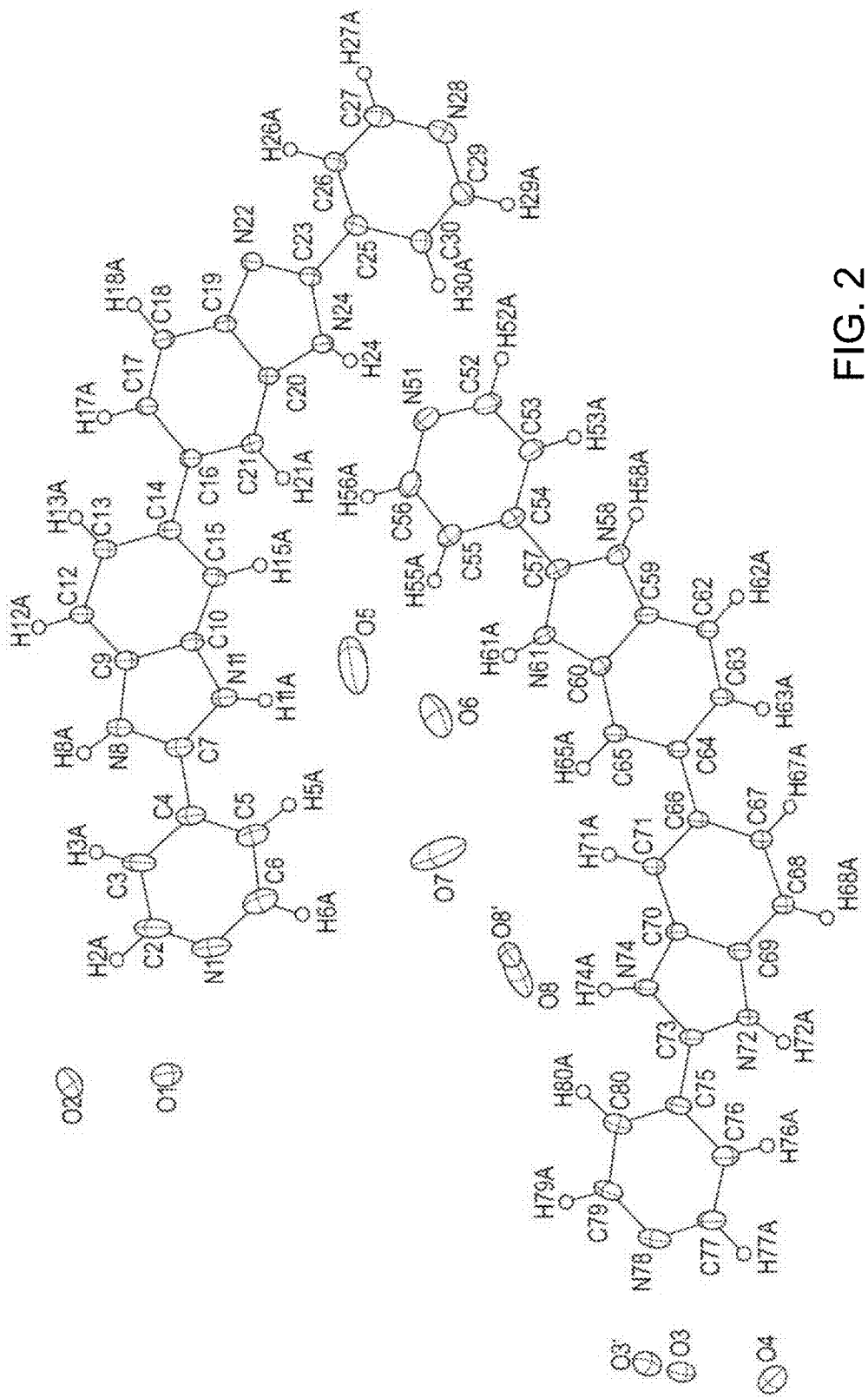
FIG. 2 shows an ORTEP plot for the ridinilazole and water molecules of the Form A structure.
Figure 3:
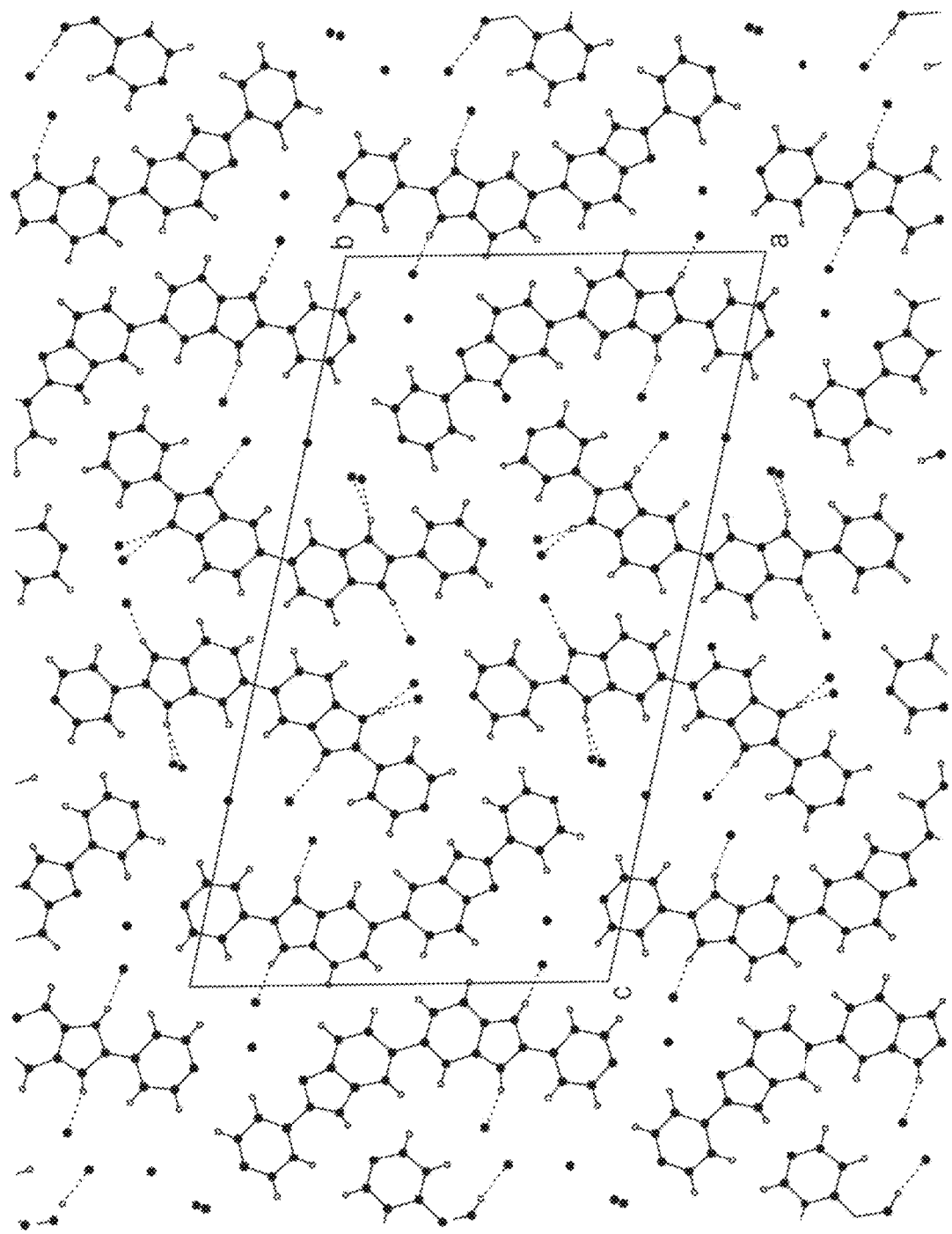
FIGS. 3-5 show packing diagrams for the ridinilazole tetrahydrate Form A structure along each crystallographic axis.
Figure 4:
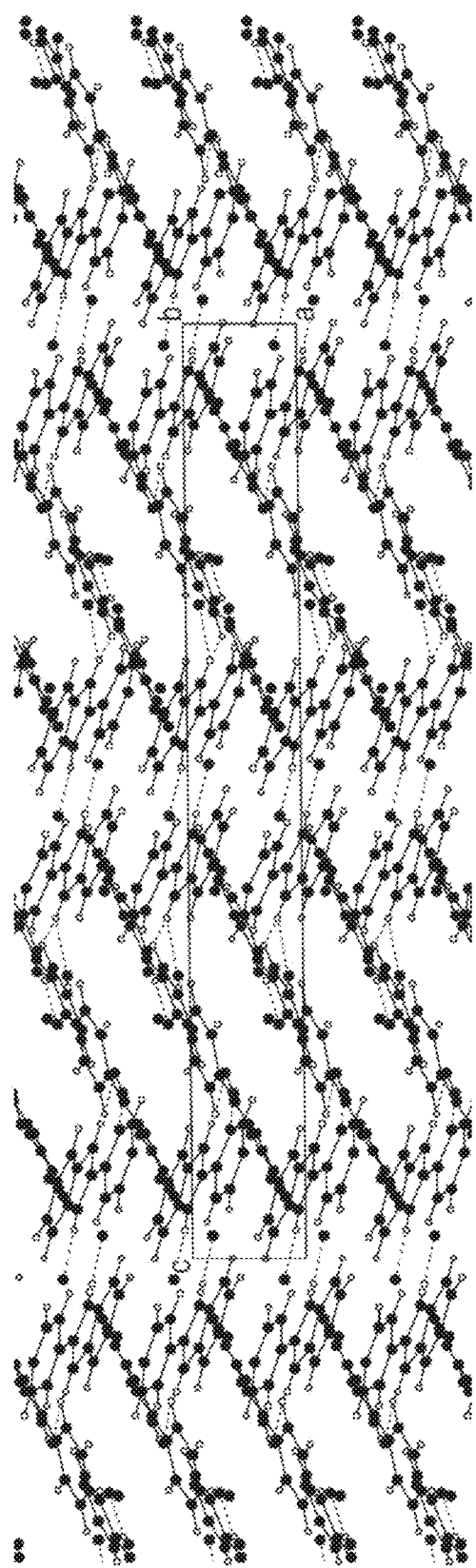
Figure 5:
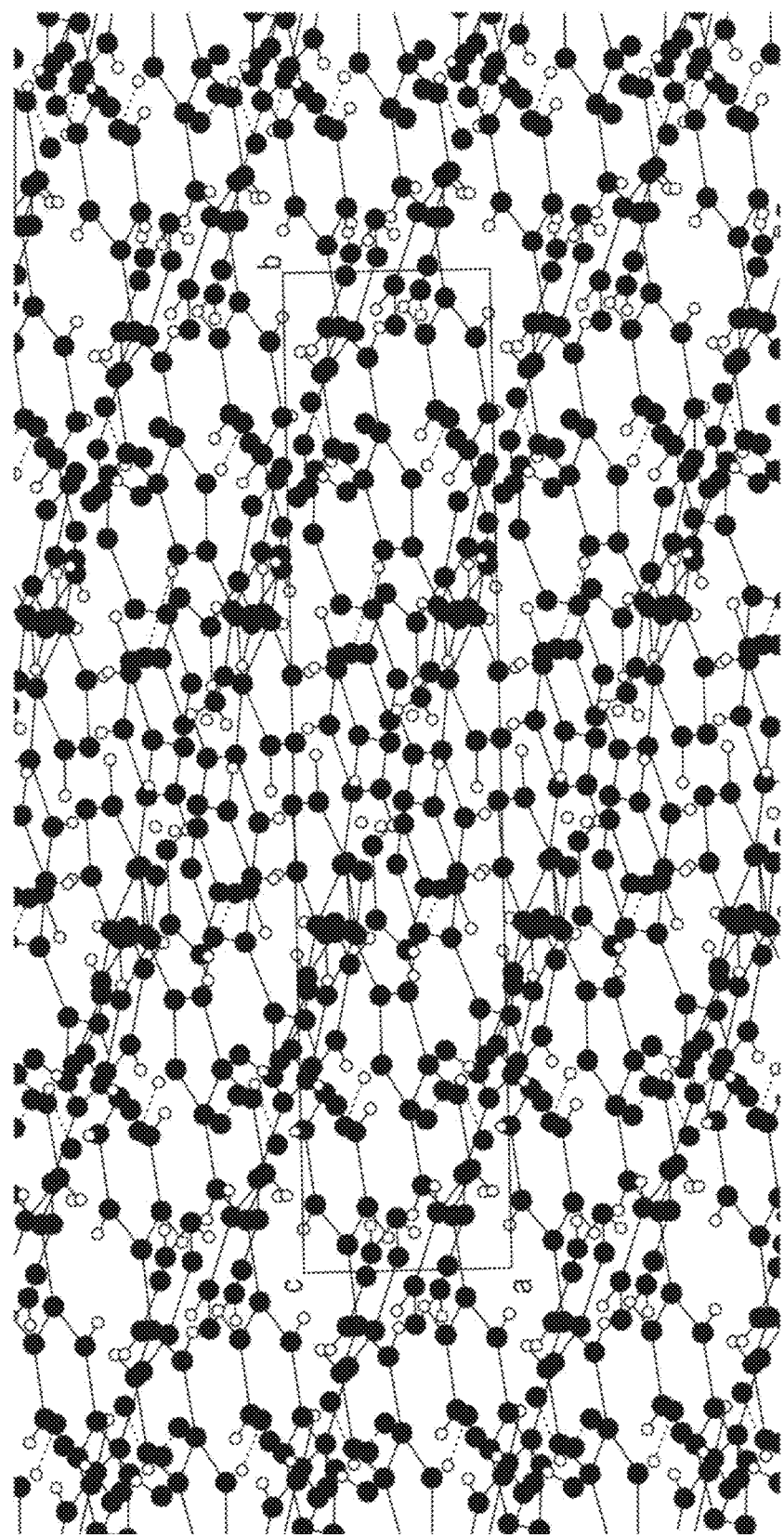

An atom numbering scheme for the ridinilazole and water molecules is displayed in FIG. 2 as an ORTEP plot. Packing diagrams for the ridinilazole Form A structure are displayed in FIG. 3 to FIG. 5 and are shown along each crystallographic axis. Hydrogen bonding between ridinilazole molecules cannot be described as only one hydrogen bond between N24-H24 . . . N51 can be clearly located. The other hydrogen bonds occurring in the structure are formed between the water molecules, imidazole hydrogens and pyridine nitrogen atoms. However due to the large disorder of water molecules and their hydrogen atoms the hydrogen bond network cannot be fully resolved.

Example 3: Production of Ridinilazole Form D

Reaction: The reaction flask was charged with 4-cyanopyridine (0.85 kg), and MeOH (5.4 kg) and NaOMe as 30 wt % solution in MeOH; 0.5 eq; 0.15 kg (NAM-30) was dosed in. The resulting mixture was heated at 60° C. for 10 min. and then cooled. This solution was added to a mixture of DAB (0.35 kg) and acetic acid (0.25 kg) in MeOH (1 l) at 60° C. in 1 h. The mixture was then heated for 2 h. The reaction mixture was allowed to cool to ambient temperature overnight. The crystalline mass was filtered and washed with MeOH (1.4 L) and sucked dry on the filter.

Purification: The Norit® treatment was conducted 4 times.

Figure 6:
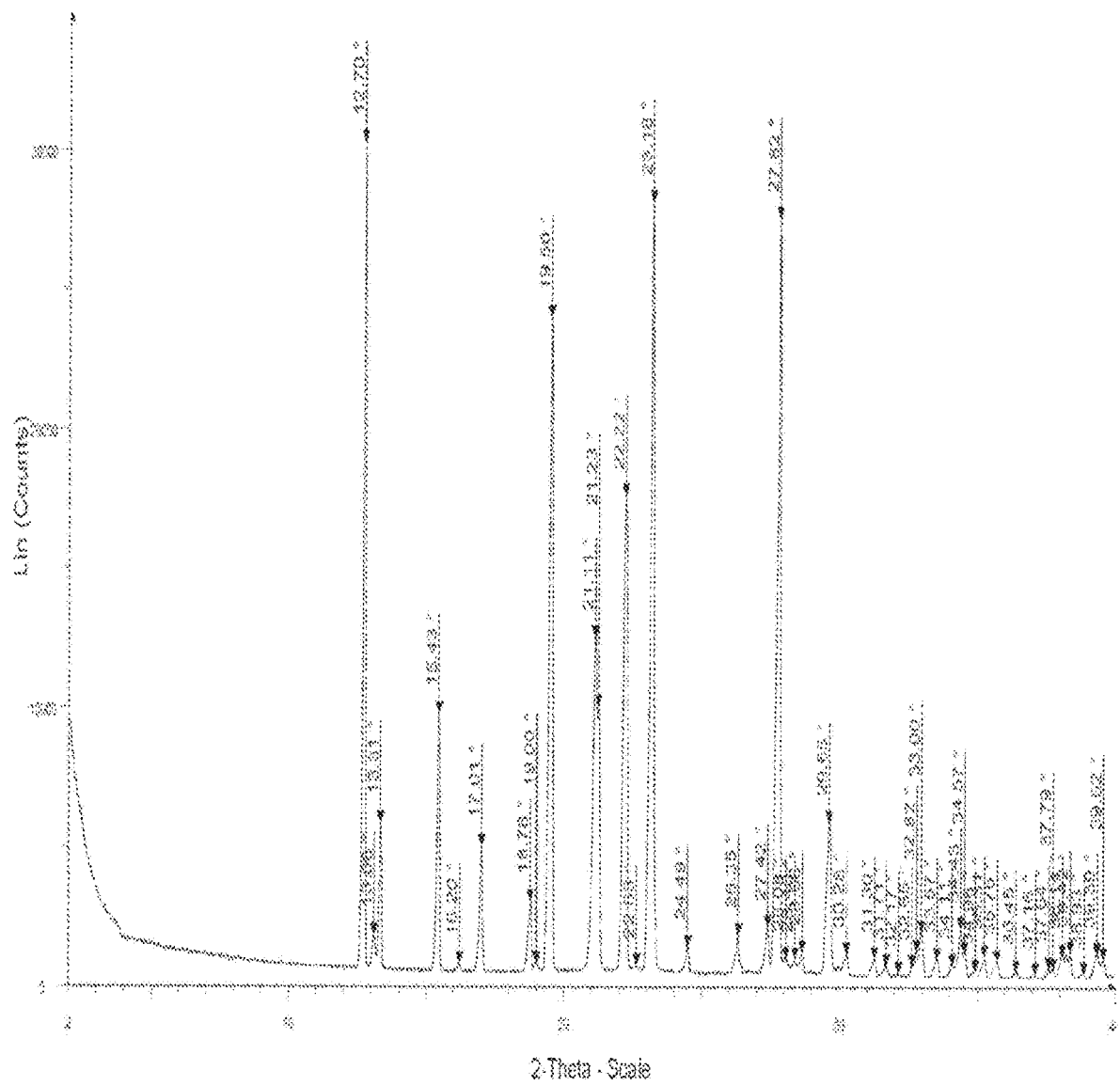
FIG. 6 shows a representative x-ray powder diffraction pattern for ridinilazole anhydrate Form D.

XRPD analysis showed that this process yielded ridinilazole anhydrate Form D (see FIG. 6). The reflections are shown in Table 2, below:

TABLE 2

Ridinilazole Tetrahydrate Form
D 2-Theta °
Angle 2-Theta °
(Form D)

12.7
13.08
13.31
15.43
16.2
17.01
18.78
19
19.5
21.11
21.23
22.22
22.63
23.18
24.49
26.35
27.42
27.82
28.08
28.4
28.66
29.65
30.28
31.3
31.71
32.17
32.65
32.82
33
33.57
34.11
34.43
34.57
34.96
35.31
35.76
36.45
37.16
37.64
37.79
38.14
38.42
38.93
39.39
39.62

Example 4: Crystal Structure of Ridinilazole Anhydrate Form D

Single crystals of ridinilazole Form D were grown via vapour diffusion at RT of a solution of ridinilazole in ethanol using water as antisolvent and were submitted for single crystal structure determination. A prismatic crystal specimen, approximate dimensions 0.3 mm×0.2 mm×0.1 mm, was used for the X-ray crystallographic analysis.

Figure 7:
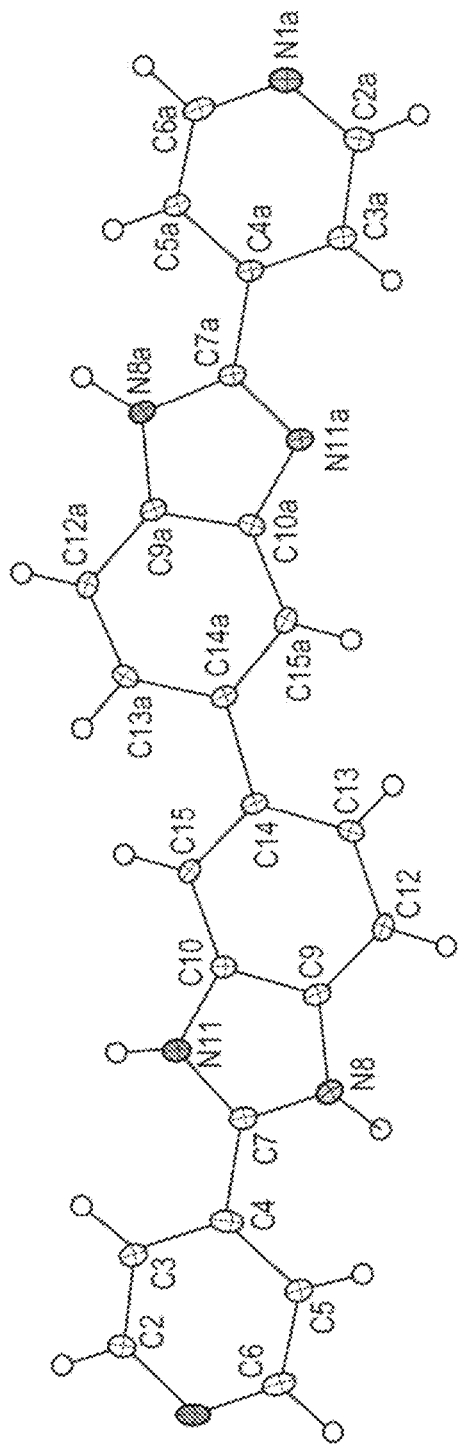
FIG. 7 shows an ORTEP plot for the ridinilazole molecule of the Form D structure.
Figure 8:
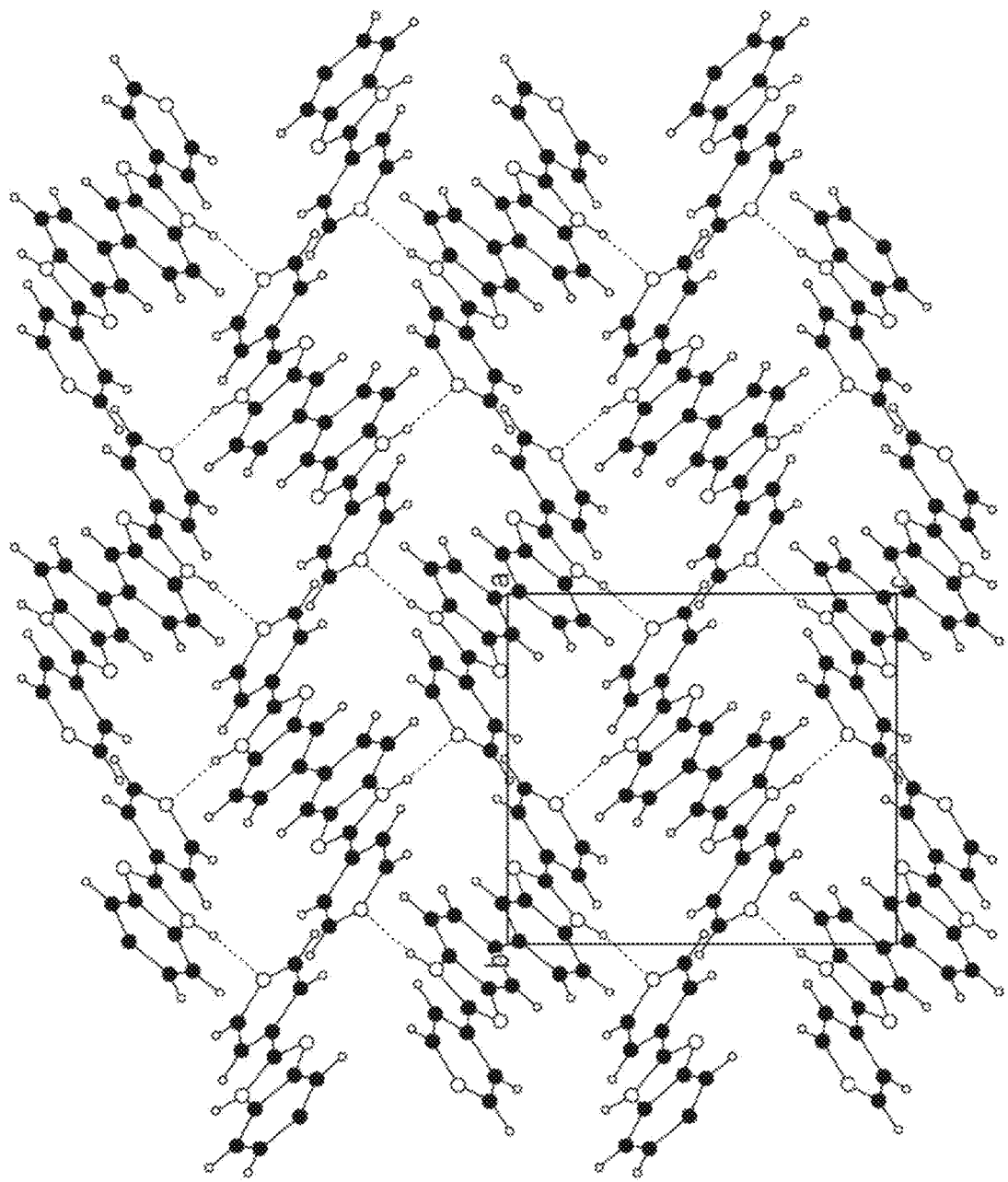
FIGS. 8-10 show packing diagrams for the ridinilazole Form D structure along each crystallographic axis.
Figure 9:
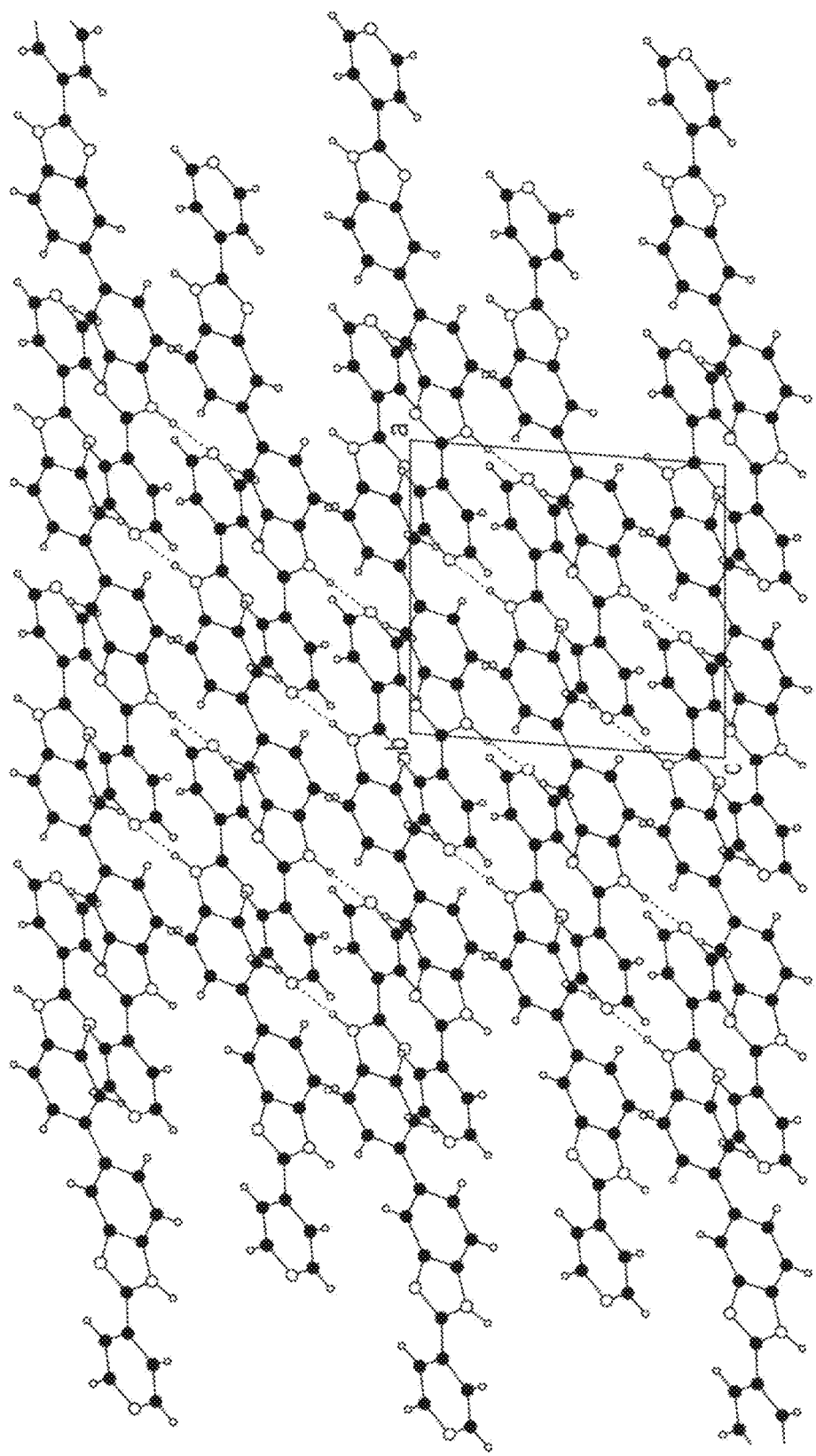
Figure 10:
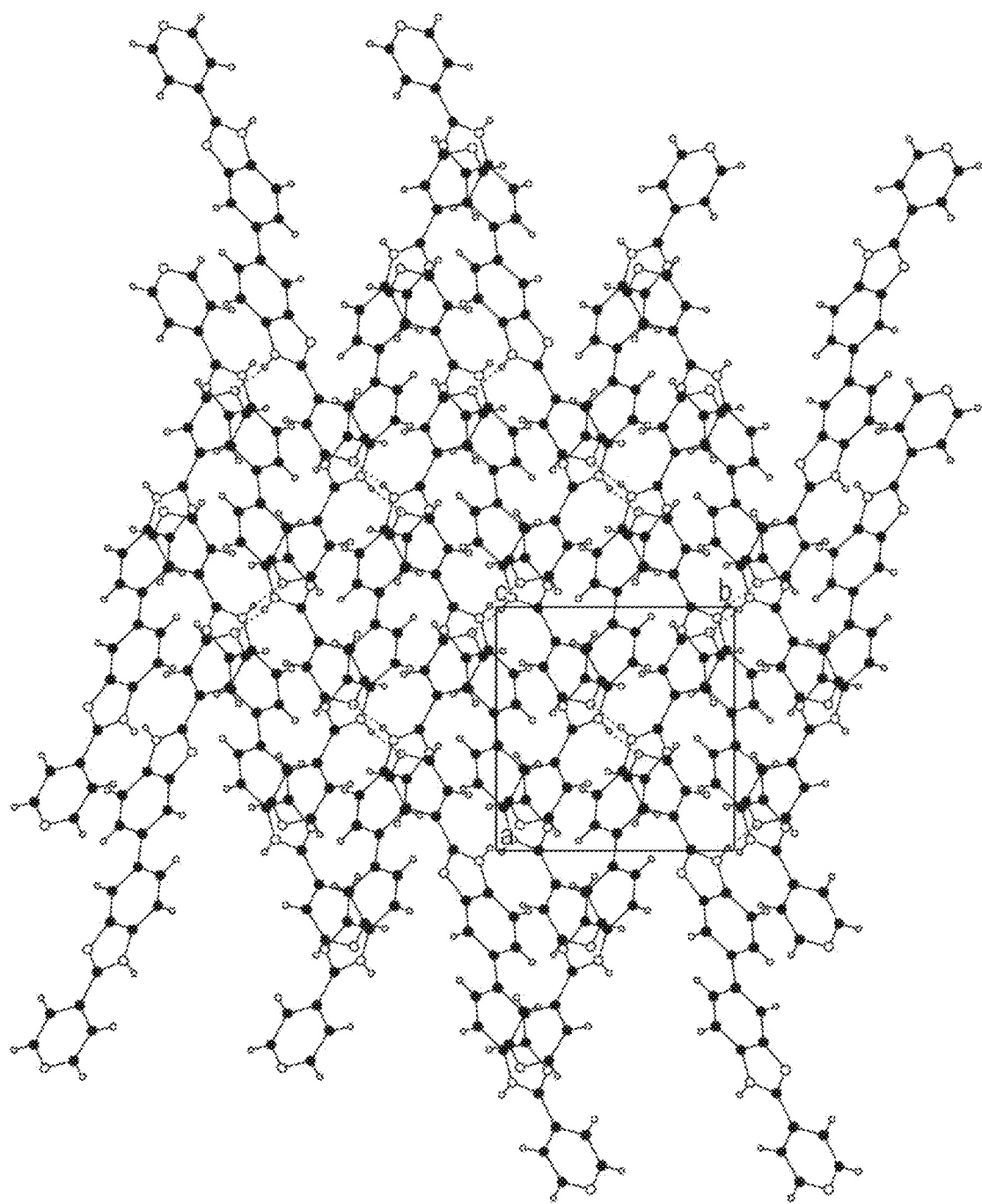
Figure 11:
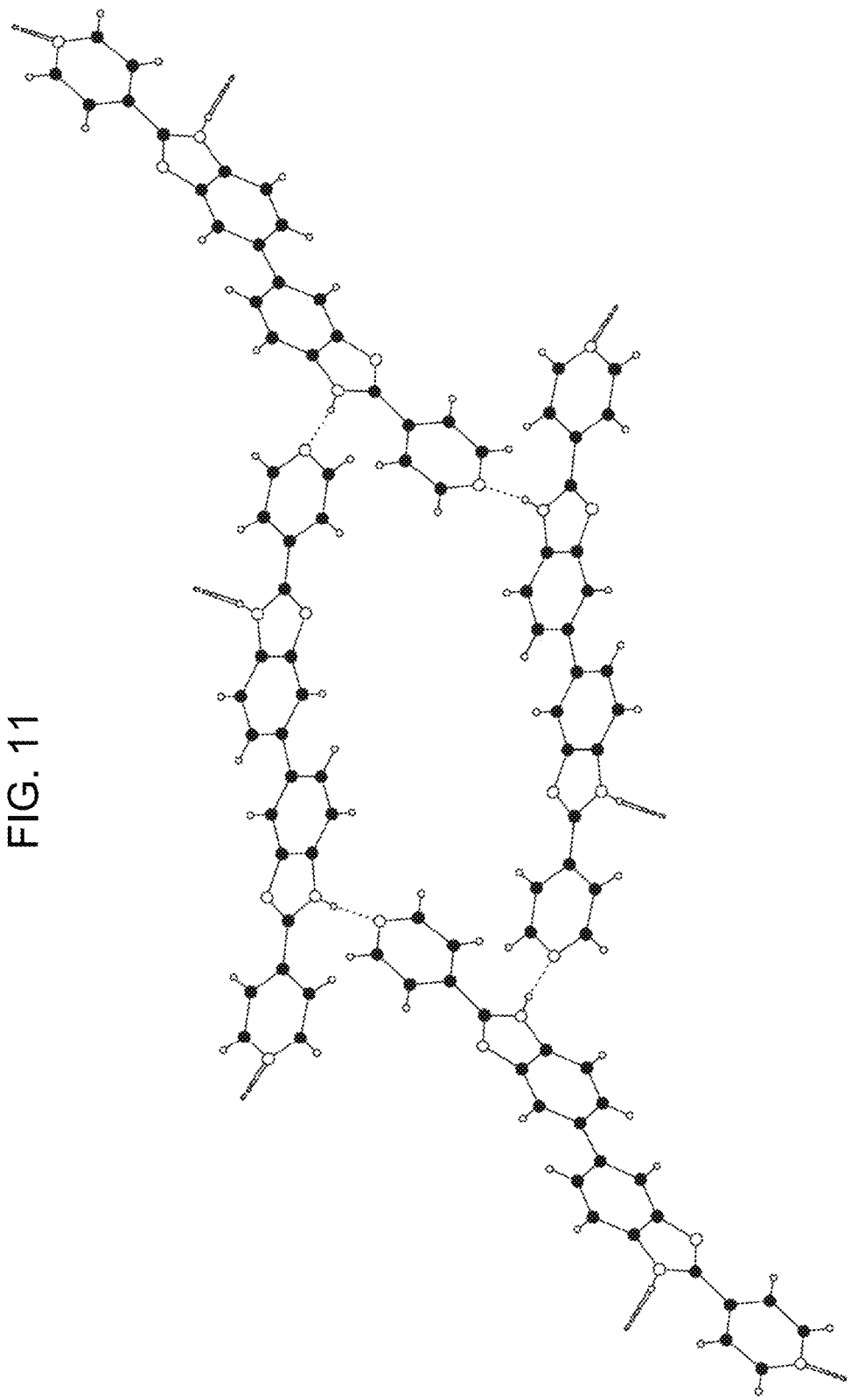
FIG. 11 shows hydrogen bonding between ridinilazole Form D molecules generating a two dimensional network along the ab plane (i.e. as viewed along the c axis).

The structure was solved by routine automatic direct methods and refined by least-squares refinement on all unique measured F2 values. The numbering scheme used in the refinement is shown in FIG. 7. An atom numbering scheme for the ridinilazole molecule is displayed in FIG. 7 as an ORTEP plot. Packing diagrams for the ridinilazole Form D structure are displayed in FIGS. 8-10 and are shown along each crystallographic axis. Hydrogen bonding between ridinilazole molecules generate a two dimensional network along the ab plane (see FIG. 11). The hydrogen bonds are formed between the donating hydrogen imidazole nitrogen atoms and the accepting pyridine nitrogen atoms. The network is expanded in the third direction through weaker interaction between hydrogens atoms and it electrons of aromatic carbons.

Example 5: Conversion of Ridinilazole Form D to Form A

Ridinilazole Form D is prepared as described in Example 3. Ridinilazole Form A is prepared as described in Example 1. Seed crystals were prepared by hand grinding and sifting. The conversion was carried out as follows:
1) Charge Form D.
2) Charge MeOH.
3) Heat to 60° C. Stirred 300 rpm.
4) Hold 15 min.
5) Charge Water over 30 min, $a_w$~0.47
6) Cool to 40° C. over 2 h.
7) Seeded with 2 wt % Form A (or with 2 wt % Form A in a slurry prepared in MeOH/H$_2$O (80/20 v/v) and slurried for 2.5 h before addition)
8) Wait 1 h. Thick slurry, limited mobility.
9) Cool to 20° C. over 2 h.
10) Heat to 40° C. over 4 h.
11) Cool to 20° C. over 10 h.
12) Wait 2.5 h. Thick, mobile slurry.
13) VF. Filtration time: 15 sec.
14) Wash reactor 3× with 1 vol MeOH/H$_2$O (80/20 v/v), 3 ml each wash. Wash wet cake with 1 vol MeOH/H$_2$O (80/20 v/v), 3 ml.

Example 6: Ridinilazole 200 mg Oral Tablet

Preferred tablet formulations are set forth in Tables 3 and 4, below.

TABLE 3

| Manufacturing Operation & Component | Component Function | Unit Quantity (mg) | % Formula (% w/w) |
|---|---|---|---|
| Intragranular Phase | | | |
| Ridinilazole Tetrahydrate (Form A) | Active | 200.001 | 50.00 |
| Lactose monohydrate 200M | Diluent | 101.96 | 25.49 |
| Microcrystalline Cellulose (Avicel PH101) | Diluent | 38.04 | 9.51 |
| Hydroxypropylcellulose | Binder | 12.00 | 3.00 |
| Croscarmellose sodium | Disintegrant | 8.00 | 2.00 |
| Purified water * Fluid | Granulating | q.s. | — |
| Extragranular Phase | | | |
| Lactose monohydrate 100M | Diluent | 17.48 | 4.37 |
| Microcrystalline Cellulose (Avicel PH102) | Diluent | 6.52 | 1.63 |
| Croscarmellose sodium | Disintegrant | 12.00 | 3.00 |
| Magnesium stearate | Lubricant | 4.00 | 1.00 |
| TOTAL | | 400.00 | 100.00 |
| Coating | | | |
| Opadry II Brown ** | Film Coat | 12.00 | 3.00 (w/w) |
| TOTAL | | 412.00 | N/A |

1. The quantity 200 mg of Ridinilazole Tetrahydrate (Form A) is equivalent to 169 mg of ridinilazole content on an anhydrous basis.
* Purified water is removed during intermediate drying.
** Film-coat is applied as an aqueous solution at a concentration of 20% w/v..

TABLE 4

| Component | Component Function | Quantity (mg) |
|---|---|---|
| Intragranular Phase | | |
| Ridinilazole tetrahydrate Form A[2] | API | 200.00 |
| Lactose monohydrate 200M | First diluent | 101.96 |
| Microcrystalline Cellulose (Avicel PH101) | First diluent | 38.04 |
| Hydroxypropylcellulose | Binder | 12.00 |
| Croscarmellose sodium | First disintegrant | 8.00 |
| Purified Water | | —* |
| Extragranular Phase | | |
| Lactose monohydrate 100M | Second diluent | 17.48 |
| Microcrystalline Cellulose | Second diluent | 6.52 |
| Croscarmellose sodium | Second disintegrant | 12.00 |
| Magnesium stearate | Lubricant | 4.00 |
| TOTAL | | 400.00 |
| Coating | | |
| Opadry II Yellow 33G220012 | Film Coat | 12.00 |
| Purified Water | | —* |
| TOTAL | | 412.00 |

1. The quantity 200 mg of Ridinilazole Tetrahydrate (Form A) is equivalent to 169 mg of ridinilazole content on an anhydrous basis.
*Purified water is removed during intermediate drying.

XRPD analysis was carried out on the ridinilazole tablet to confirm no form change occurred after tableting. One tablet was crushed with a pestle and mortar and analysed by transmission XRPD. Small amounts of the sample coating could not be isolated completely from the crushed sample.

Figure 12:
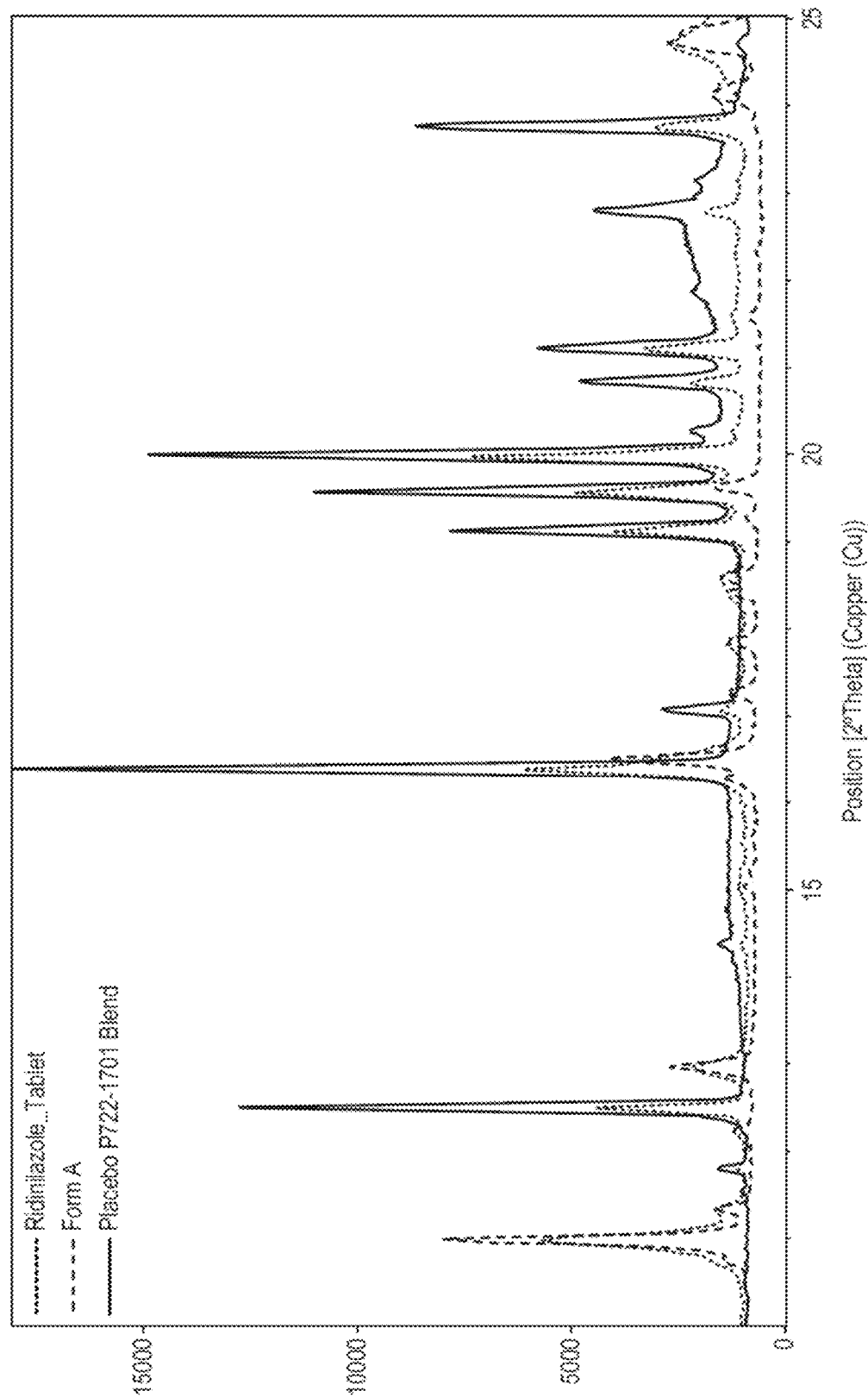
FIG. 12 shows an XRPD overlay of ridinilazole tablet (upper trace), placebo (middle trace) and Form A (lower trace) between about 10° 2 Theta and about 25° 2 Theta.

The XRPD trace showed that while the sample compared to Form A with a small amount of peak shifting, there were extra peaks present at ~12.5° 2Theta and from ~19-24° 2Theta. XRPD analysis of ridinilazole tablet, ridinilazole Form A and placebo blend confirmed these extra peaks were due to the placebo mixture (FIG. 12) i.e. the extra peaks were present in the placebo mixture and so were due to the excipient.

The stability of the ridinilazole crystal form within the tablet as packaged in the intended commercial packaging configurations. Assessments have been made using a validated discriminatory X-ray powder diffraction (XRPD) method developed as a limit test for detecting Forms D and N within the drug product. No form conversion is detected, and therefore the Form A is stable in the tablet in the proposed storage condition in the proposed commercial packaging configuration.

Example 7: Comparison of the Release and Colonic Delivery Profiles of Ridinilazole Capsule and Tablet Formulations in the In Vitro Dynamic GI Model TIM-1

The release and colonic delivery profiles of the ridinilazole 200 mg capsule and 200 mg tablets formulation were also compared in the in vitro dynamic GI model TIM-1. TIM-1 is a dynamic, multi-compartmental and predictive in vitro system that simulates the digestive conditions in the lumen of the gut (Minekus M. (2015) The TNO Gastro-Intestinal Model (TIM). In: Verhoeckx K. et al. (eds) The Impact of Food Bioactives on Health. Springer, Cham. https://doi.org/10.1007/978-3-319-16104-4_5). Simulated conditions include gastric and small intestinal transit, flow rates and composition of digestive fluids, pH, and removal of water and metabolites. TIM-1 consists of four compartments (stomach, duodenum, jejunum and ileum) and can simulate fed or fasted conditions.

Both ridinilazole formulations were tested under simulated fasted state conditions and analysed throughout the time-course of the experiment from each compartment and ileal effluent. For compartmental analyses, dialysate samples were taken from each compartment (stomach, jejunum, ileum) at 60-minute intervals.

Figure 13:
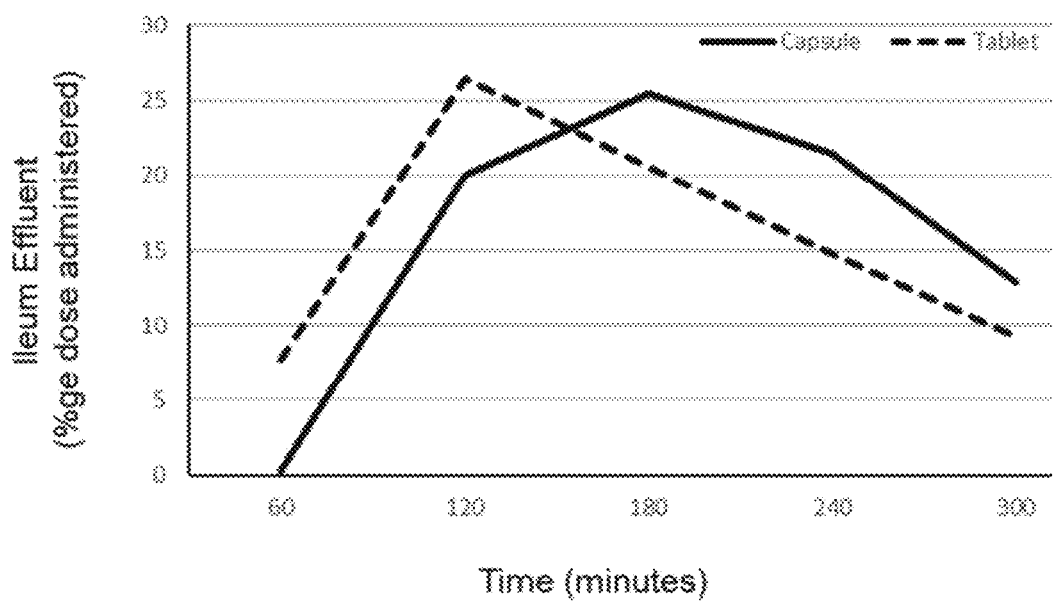
FIG. 13 shows comparative ileum effluent profiles for the ridinilazole tetrahydrate 200 mg capsule and ridinilazole tetrahydrate 200 mg tablet [each equivalent to 169 mg of anhydrous ridinilazole in the TIM-1 model gut system. The plot depicts the quantity of ridinilazole measured within the ileum effluent at each 60-minute timepoint over the duration of the experiment. The ileum effluent equates to amount of material delivered to the colon.

It was surprisingly found that the capsule formulation disintegrated more slowly than the tablet formulation, resulting in a delayed $T_{MAX}$ for measured ridinilazole in the ileal effluent relative to the tablet formulation (FIG. 13). For the tablet formulation the highest amount of ridinilazole was measured in the 60-120 minutes time period whereas for the capsule formulation in the 120-180 minutes time period.

Example 8: Comparison of the In Vivo Release Profiles of Ridinilazole Capsule and Tablet Formulations A single dose pharmacokinetic (PK) study evaluated the ridinilazole Phase 2 liquid capsule formulation and the ridinilazole solid tablet formulation of the invention in dog. Groups of 3 animals were administered test articles as a single dose (200 mg) with blood samples taken 8 hours post dose. All bioanalysis results were below the limit of quantification and there were no adverse effects of either formulation in the test subjects.

Example 9: Particle Size

As a material with very low aqueous solubility and relatively poor wettability, control of drug substance particle size is important in controlling variability in the processability and performance of the process thereby providing control over granule structure and thereby tablet quality.

The particle size of ridinilazole is controlled within the drug substance; particle size reduction of ridinilazole crystal agglomerates occurs as the last step in drug substance manufacture (see Example 1). This not only ensures batch-to-batch consistency of particle size distribution within the drug substance but also assures batch-to-batch consistency in both manufacture and quality of the ridinilazole drug product.

Figure 14:
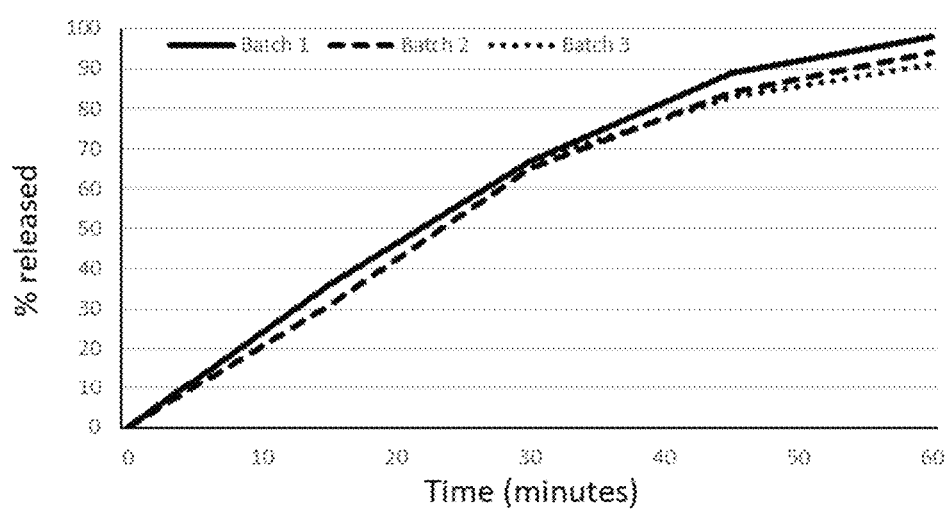
FIG. 14 shows the dissolution profiles for tablets with drug substance at limits of particle size specification.

The suitability of the proposed commercial specification range for the particle size-reduced drug substance ($D_{90}$ 10-20 μm) in relation to drug product manufacturing and performance has been assessed. Ridinilazole tablets have been manufactured using drug substance batches at the limits of the proposed specifications (Table 4). FIG. 14 shows the dissolution profiles from these batches that demonstrate the proposed drug substance particle size specification limits are appropriate for drug product manufacture and performance.

TABLE 5

| | Input Drug Substance | | |
|---|---|---|---|
| | Particle Size | | |
| Batch ID | $D_{90}$ μm | $D_{50}$ μm | $D_{10}$ μm |
| 1 | 20 | 7 | 2 |
| 2 | 11 | 5 | 1 |
| 3 | 11 | 5 | 1 |
| 4 | 10 | 3 | 1 |

Ridinilazole tablets manufactured using drug substance with crystal agglomerate particles having a $D_{90}$ outside of the 10-20 μm range (and in particular having a $D_{90}$ below 4 μm or above 30 μm, and also in particular having a $D_{90}$ above 40 μm) yielded material for tableting having properties which were unsuitable for drug product manufacture and performance.

Additional studies were completed to evaluate the particle size of the micronized ridinilazole tetrahydrate to be used in tablet formulations. The data is provided in Table 6 below:

| Batch ID | $D_{90}$ μm | $D_{50}$ μm | $D_{10}$ μm |
|---|---|---|---|
| 1 | 14 | 6 | 1.5 |
| 2 | 11 | 5 | 1.1 |
| 3 | 14 | 7 | 1.7 |
| 4 | 13 | 6 | 1.5 |
| 5 | 14 | 7 | 2.0 |

According to one embodiment of the present invention, the ridinilazole tetrahydrate crystal agglomerates used to manufacture ridinilazole tetrahydrate 200 mg tablets have particle sizes within the ranges: $D^{90}$ between about 10 μm and about 20 μm, $D^{50}$ between about 2 μm to about 9 μm, and $D^{10}$ below 2 μm. According to other embodiments, the ridinilazole tetrahydrate crystal agglomerates have particle sizes within the ranges: $D^{90}$ between 8 μm and 15 μm, $D^{50}$ between 2 μm and 8 μm, and $D^{10}$ below 2 μm.

Example 10: Manufacturing Process

Ridinilazole tablets (200 mg) were prepared as described below:

Wet Granulation

After screening into the high shear granulator bowl, batch quantities of ridinilazole (Form A), lactose monohydrate, microcrystalline cellulose, hydroxypropylcellulose and croscarmellose sodium for the wet granulation, intragranular phase are subject to an initial short premixing of approximately 1 minute at 80 revolutions per minute (rpm).

With continued mixing, purified water is added. At 12% by weight of added water and at 24% by weight of added water the wet mass is transferred manually through a 2000 μm screen to improve water distribution, each time being returned to the granulator bowl to continue granulation. At approximately 35% by weight added water the wet granules are transferred into a fluid bed dryer.

Drying

The wet milled granules are then transferred to a fluid bed dryer at an inlet air temperature of approximately 60° C.

until the target limit of detection (LOD) is achieved. Upon completion of the drying. The dried granules are transferred through a Comil equipped with 1143 μm screen into an appropriately sized blender bin.

Final Blending

Dried milled granules are combined with lactose monohydrate, microcrystalline cellulose and croscarmellose sodium for the extra granular phase.

Lubrication

The calculated batch quantity of magnesium stearate is added to the dry blend and then transferred manually through a 250 micrometer screen into the 20 L bin containing the final blend. Lubrication is performed by tumbling the 20 L bin in the blender for 2 minutes at 30 rpm.

Compression

Tablets are compressed using oval shaped tooling. Dedusting and metal checking are performed in line post compression.

Coating

Tablet cores are coated in a pan coater with Opadry® II Yellow. Target weight gain for coated tablets is 3 to 4%.

Example 11

Effect of Micronization on the Tabletting Properties of Ridinilazole API

The effect of micronization on the tableting properties of Ridinilazole API has been examined on two separate occasions during the development process.

Tablets produced with micronized and unmicronized API were first compared during a formulation development study. Tablets were compressed with both round and capsule shaped tooling and the dissolution profiles were compared (FIG. 16).

The tablets manufactured with the unmicronized API demonstrated slower and incomplete dissolution. The disintegration times were also extended.

The second occasion that the effect of micronization was studied was during a

Process Understanding campaign. In this study a batch of tablets was manufactured using the finalized formulation and process. The unmicronized material demonstrated different behavior during the wet granulation process. In the standard process 945 g water is added to the powder at a rate of 200 g/min. After 4 minutes of water addition the granule already appeared to be completely granulated. A portion of the granulate was removed at this stage for evaluation and then the remainder of the granulation was taken to completion.

During compression there were differences noted—the tablets are typically compressed to a target hardness of 17.5 kp. It was not possible to achieve this target hardness using the maximum compression pressure of the table machine. Tablets were produced at hardnesses of 7.7 kp and 12.9 kp for the two sub-lots.

Figure 17:
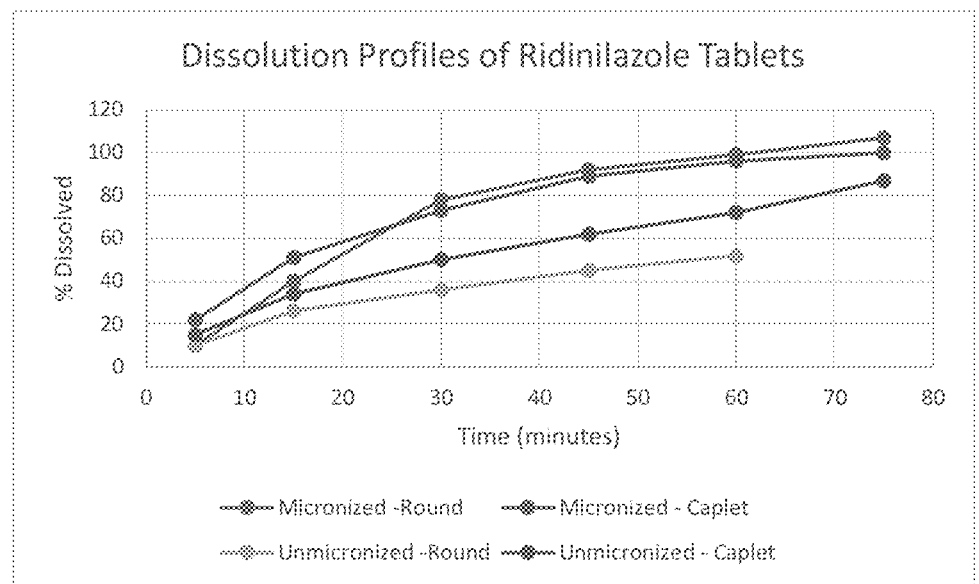
FIG. 17 illustrates dissolution profiles of ridinilazole tetrahydrate tablets for micronized and unmicronized tablets and caplets.
Figure 18:
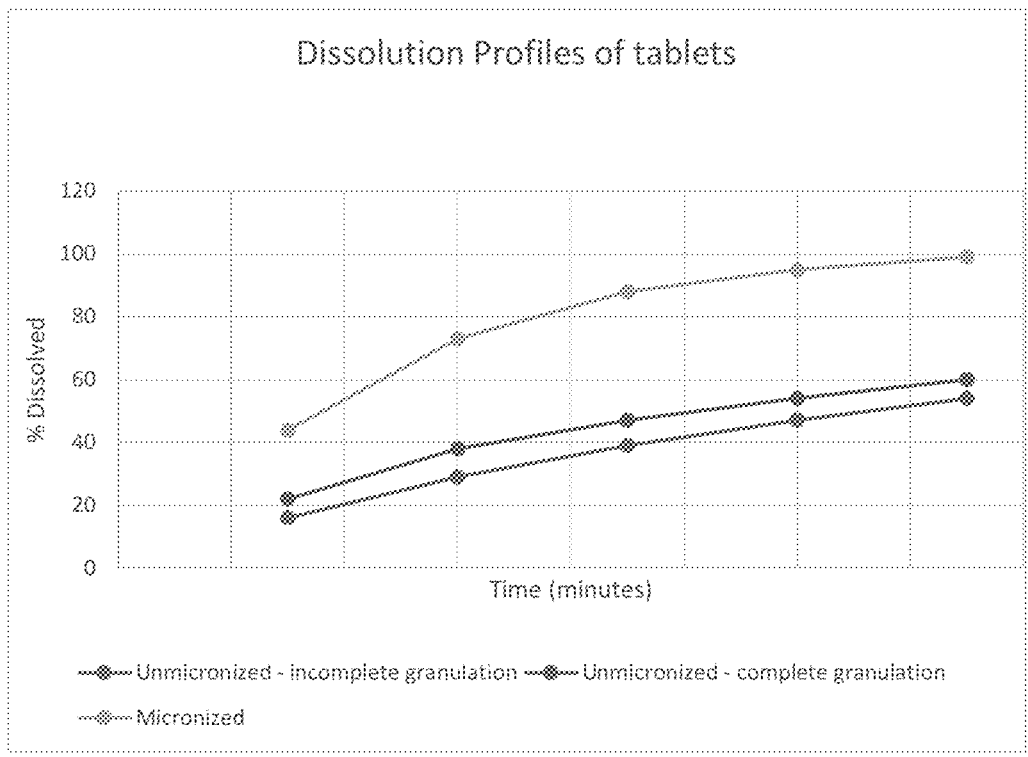
FIG. 18 illustrates dissolution profiles of ridinilazole tetrahydrate tablets for unmicronized tablets—incomplete granulation, unmicronized tablets—complete granulation, and micronized tablets.

The dissolution profiles of the unmicronized batches mirrored those in the earlier studies. When compared to batches manufacture by the same process using micronized API there was a significant drop in both the rate and extent of dissolution. (FIG. 17).

Example 12—Formulation Development

The objective of this study was to develop a formulation and process for ridinilazole tetrahydrate drug substance, compressed into a tablet at 200 mg strength. Table 7 provides a summary of the components to produce a tablet which meets the desired specification targets with respect to disintegration dissolution and manufacturability and produced a robust formulation for scale up.

TABLE 7

Ridinilazole Tetrahydrate Formulation for Manufacturing

| Material | Dosage (mg) | Percentage Formula (% w/w) |
|---|---|---|
| Intra granular | | |
| Ridinilazole tetrahydrate | 200.00 | 50.000 |
| Lactose monohydrate 200M | 79.86 | 7.485 |
| Avicel PH101 | 11.14 | 2.786 |
| HPC Klucel EXF | 12.00 | 3.000 |
| Croscarmellose sodium | 8.00 | 2.000 |
| Granulating Fluid: 35% | | |
| Purified water | q.s | 35% of batch Size |
| Extra granular | | |
| Lactose monohydrate 200M | 89.68 | 22.395 |
| Avicel PH101 | | |
| Croscarmellose sodium | 12.00 | 3.000 |
| Magnesium stearate | 4.00 | 1.000 |
| Total | 400.00 | 100.000 |

Wet granulation was used to manufacture the batches. An exemplary process is illustrated in FIG. 19.

Figure 20:
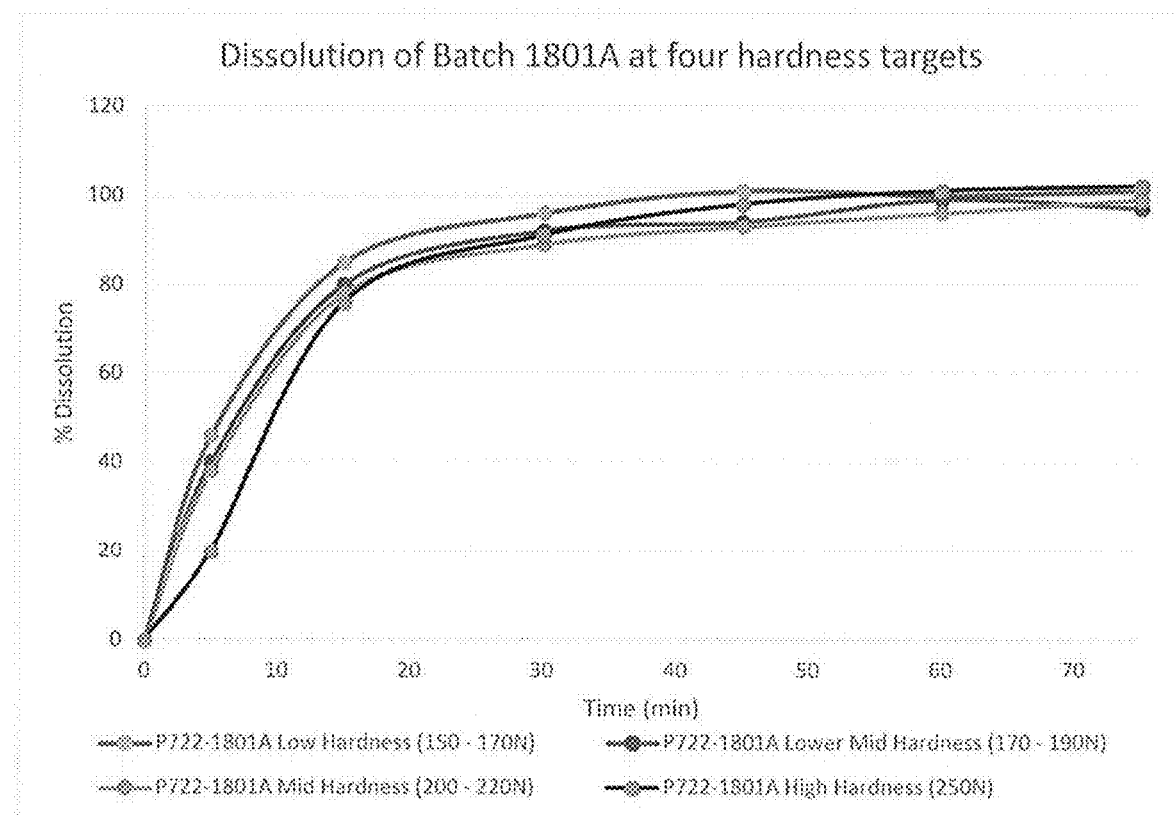
FIG. 20 illustrates dissolution at four different hardness targets.

A batch (1801A) was compressed to generate two different hardness targets (150-170 N, 170-190 N, 200-220 N, and 250 N). FIG. 20 reveals the impact of hardness on drug release at the 5 min time point, where harder tablets are associated with slower release; however, tablets at all four hardness levels release the drug completely by 50 minutes.

The longer disintegration time at hardness 250 N was expected and this is due to the harder tablets being less porous and therefore longer time for water ingress. The manufacture generated tablets with low friability for hardness targets.

Figure 21:
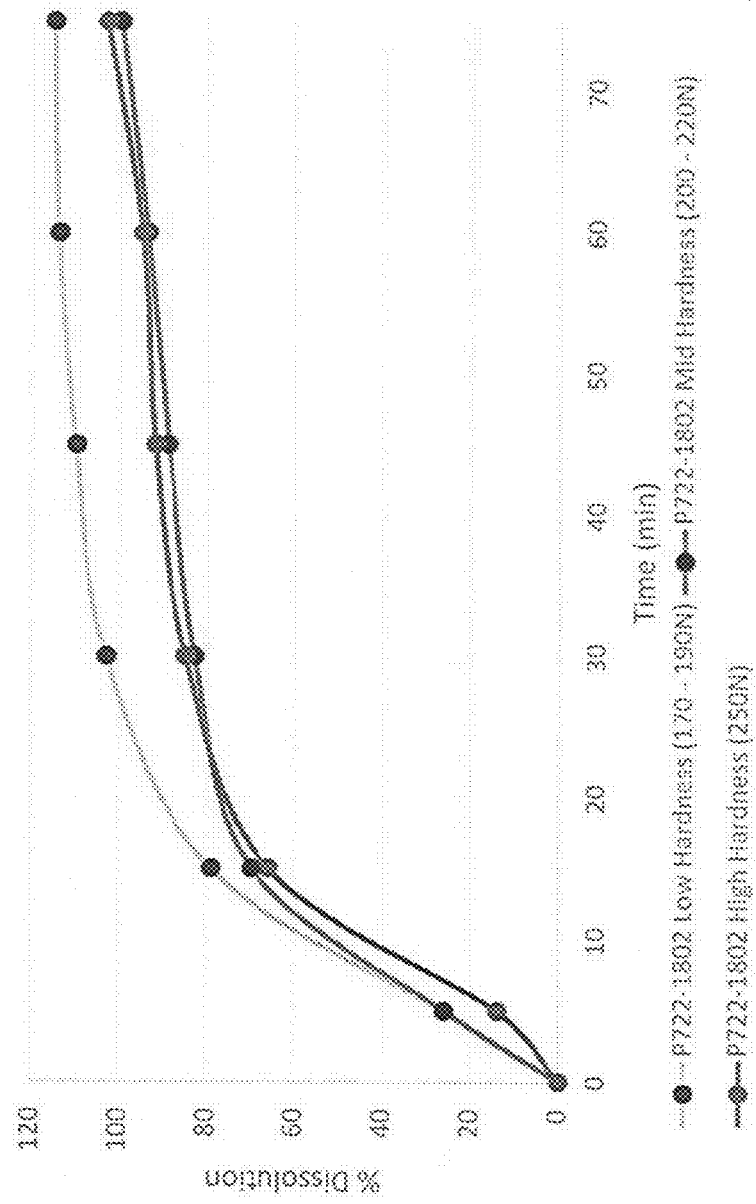
FIG. 21 illustrates dissolution at three different hardness targets.

Drug release for hardness values of 200-220 N and 250 N follows a largely similar pattern and it reaches completion by 75 mins. In contrast, the release of tablets with hardness 170-190 N reaches 103% at 30 minutes. The results are illustrated in FIG. 21.

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

What is claimed is:

1. A tablet formulation comprising:
   (i) ridinilazole crystal agglomerates; and
   (ii) an intragranular solid phase incorporated in an extragranular solid phase, wherein:
      (a) the intragranular phase comprises ridinilazole crystal agglomerates having a particle size $D_{90}$ of 4 to 30 μm dispersed within a first pharmaceutically acceptable excipient system; and
      (b) the extragranular phase comprises a second pharmaceutically acceptable excipient system,
   wherein the ridinilazole crystal agglomerates comprise ridinilazole Form A characterized by a powder X-ray diffractogram (XRPD) comprising characteristic peaks at 2-Theta angles of $(11.02\pm0.2)°$, $(16.53\pm0.2)°$ and $(13.0\pm0.2)°$.

2. The tablet formulation of claim 1, wherein the ridinilazole Form A comprises ridinilazole tetrahydrate Form A.

3. The tablet formulation of claim 1, wherein the ridinilazole Form A has a particle size $D_{90}$ of about 7 to about 25 μm.

4. The tablet formulation of claim 1, wherein the ridinilazole Form A has a particle size $D_{90}$ of about 10 to about 20 μm.

5. The tablet formulation of claim 1, wherein the ridinilazole Form A is present in the tablet at a amount of up to 40%, 45%, 50%, 55%, 60%, 65%, 70%, 75% or 80% wt/wt.

6. The tablet formulation of claim 1, wherein the ridinilazole Form A is present in the tablet at a concentration≥40% wt/wt.

7. The tablet formulation of claim 1, wherein the intragranular phase is present in the tablet at a concentration of about 65 to about 95% wt/wt.

8. The tablet formulation of claim 1, wherein the extragranular phase is present in the tablet at a concentration of about 5 to about 35% wt/wt.

9. The tablet formulation of claim 1, wherein the first excipient system is present in the tablet at a concentration of up to about 40% wt/wt.

10. The tablet formulation of claim 9, wherein the first excipient system comprises a first diluent, and wherein the first diluent is present in the tablet at a concentration of up to 35% wt/wt.

11. The tablet formulation of claim 10, wherein the first diluent comprises lactose monohydrate and/or microcrystalline cellulose,
wherein the lactose monohydrate is present in the tablet at a concentration of up to 30% wt/wt, and the microcrystalline cellulose is present in the tablet at a concentration of up to 10% wt/wt.

12. The tablet formulation of claim 1, wherein the first excipient system comprises a first disintegrant,
wherein the first disintegrant is selected from croscarmellose sodium, crospovidone, microcrystalline cellulose, polacrilin potassium, powdered cellulose, pregelatinized starch, sodium starch glycolate and starch.

13. The tablet formulation of claim 12, wherein the first disintegrant is present in the tablet at a concentration of up to 2% wt/wt.

14. The tablet formulation of claim 1, wherein the first excipient system comprises a binder,
wherein the binder is selected from the group consisting of polyvinyl pyrrolidone (PVP), copovidone (PVP-polyvinyl acetate copolymer), partially gelatinized starch (PGS), and cellulose ethers, wherein the cellulose ethers are selected from hydroxypropyl cellulose (HPC), methyl cellulose (MC), hydroxypropylmethyl cellulose (HPMC), ethylcellulose (EC) and sodium carboxymethyl cellulose (NaCMC).

15. The tablet formulation of claim 14, wherein the binder is present in the tablet at a concentration of up to 3% wt/wt.

16. The tablet formulation of claim 1, wherein the second excipient system is present in the tablet at a concentration of up to 10% wt/wt.

17. The tablet formulation of claim 1, wherein the second excipient system comprises a second diluent and/or a second disintegrant and/or a lubricant.

18. The tablet formulation of claim 17, wherein the second diluent is present in the tablet at a concentration of up to 6% wt/wt.

19. The tablet formulation of claim 17, wherein the second diluent comprises lactose monohydrate and/or microcrystalline cellulose, wherein
the lactose monohydrate is present in the tablet at a concentration of up to 5% wt/wt, and the microcrystalline cellulose is present in the tablet at a concentration of up to 2% wt/wt.

20. The tablet formulation of claim 1, wherein the second excipient system comprises a second disintegrant,
wherein the second disintegrant is selected from croscarmellose sodium, crospovidone, microcrystalline cellulose, polacrilin potassium, powdered cellulose, pregelatinized starch, sodium starch glycolate and starch.

21. The tablet formulation of claim 20, wherein the second disintegrant is present in the tablet at a concentration of up to 3% wt/wt.

22. The tablet formulation of claim 1, wherein the second excipient system comprises a lubricant,
wherein the lubricant is selected from: (a) fatty acids; (b) metallic salts of fatty acids; (c) combinations of fatty acids and metallic salts thereof; (d) fatty acid esters; (e) metallic salts of fatty acid esters; and (f) inorganic materials and polymers.

23. The tablet formulation of claim 22, wherein the lubricant comprises:
(i) a fatty acid selected from the group consisting of stearic acid, palmitic acid and myristic acid;
(ii) a metallic salt of a fatty acid selected from magnesium stearate, calcium stearate and zinc stearate;
(iii) a combination of stearic acid and magnesium stearate;
(iv) a fatty acid ester selected from glyceride esters and sugar esters;
(v) a glyceride ester selected from glyceryl monostearate, glyceryl tribehenate, and glyceryl dibehenate;
(vi) a sugar ester selected from sorbitan monostearate and sucrose monopalmitate; and/or
(vii) sodium stearyl fumarate or lysine,
or combinations thereof.

24. The tablet formulation of claim 22, wherein the lubricant is present in the tablet at a concentration of up to 1% wt/wt.

25. The tablet formulation of claim 1, wherein the second excipient system comprises lactose monohydrate, microcrystalline cellulose, croscarmellose sodium and magnesium stearate, and magnesium stearate.

26. The tablet formulation of claim 1, wherein the tablet contains about 100 about 400 mg of ridinilazole Form A.

27. The tablet formulation of claim 1, wherein the tablet contains about 200 mg of ridinilazole Form A.

28. The tablet formulation of claim 2, which has the following composition:

| Component | Component Function | Quantity (mg) | % Formula (% w/w) |
|---|---|---|---|
| Intragranular Phase | | | |
| Ridinilazole tetrahydrate Form A | Active | 200.00 | 50.00 |
| Lactose monohydrate 200M | First diluent | 101.96 | 25.49 |
| Microcrystalline Cellulose (Avicel PH101) | First diluent | 38.04 | 9.51 |
| Hydroxypropylcellulose | Binder | 12.00 | 3.00 |
| Croscarmellose sodium | First disintegrant | 8.00 | 2.00 |
| Extragranular Phase | | | |
| Lactose monohydrate 100M | Second diluent | 17.48 | 4.37 |
| Microcrystalline Cellulose (Avicel PH102) | Second diluent | 6.52 | 1.63 |

-continued

| Component | Component Function | Quantity (mg) | % Formula (% w/w) |
|---|---|---|---|
| Croscarmellose sodium | Second disintegrant | 12.00 | 3.00 |
| Magnesium stearate | Lubricant | 4.00 | 1.00 |
| TOTAL | | 400.00 | 100.00 |
| Coating | | | |
| Opadry II Yellow | Film Coat | 12.00 | 3.00 (w/w) |
| TOTAL | | 412.00 | N/A. |

29. The tablet formulation of claim 28, wherein some or all of the intragranular phase takes the form of inclusions embedded within a matrix formed by the extragranular phase.

30. The tablet formulation of claim 1, which exhibits a $T_{MAX}$ of less than 3 hours for ridinilazole Form A in ileal effluent as measured using the TIM-1 dynamic in vitro gastrointestinal model.

31. The tablet formulation of claim 28, which exhibits a $T_{MAX}$ of less than 2 hours for ridinilazole Form A in ileal effluent as measured using the TIM-1 dynamic in vitro gastrointestinal model.

32. The tablet formulation according to claim 1 for use in the treatment, therapy, or prophylaxis of CDI or CDAD.

33. The tablet formulation according to claim 1 for the manufacture of a medicament for use in the treatment, therapy, or prophylaxis of CDI or CDAD.

34. The tablet formulation according to claim 32, wherein 200 mg of ridinilazole Form A is administered.

35. The tablet formulation according to claim 32, wherein ridinilazole Form A is administered one or more times a day, preferably twice a day.

36. The tablet formulation according to claim 32, wherein ridinilazole Form A is administered for about 5 to 20 days, preferably about 10 days.

37. The tablet formulation according to claim 33, wherein 200 mg of ridinilazole Form A is administered.

38. The tablet formulation according to claim 33, wherein ridinilazole Form A is administered one or more times a day, preferably twice a day.

39. The tablet formulation according to claim 33, wherein ridinilazole Form A is administered for about 5 to 20 days, preferably about 10 days.

* * * * *